United States Patent
Sonnewald

(12) 
(10) Patent No.: US 6,723,898 B2
(45) Date of Patent: *Apr. 20, 2004

(54) METHODS FOR THE PREPARATION OF PLANTS WITH CHANGED SUCROSE CONCENTRATION BY TRANSFORMATION WITH A SUCROSE PHOSPHATE SYNTHASE NUCLEIC ACID

(75) Inventor: Uwe Sonnewald, Berlin (DE)

(73) Assignee: Bayer CropScience GmbH, Frankfurt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/376,045

(22) Filed: Aug. 17, 1999

(65) Prior Publication Data

US 2002/0019998 A1 Feb. 14, 2002

Related U.S. Application Data

(62) Division of application No. 08/778,656, filed on Jan. 3, 1997, now Pat. No. 5,976,869, which is a division of application No. 08/356,354, filed on Dec. 20, 1994, now Pat. No. 5,767,365, which is a continuation of application No. PCT/EP93/01605, filed on Jun. 22, 1993.

(30) Foreign Application Priority Data

Jun. 24, 1992 (DE) .......................................... 42 20 758

(51) Int. Cl.⁷ .............................. A01H 5/00; C12N 5/14; C12N 15/82
(52) U.S. Cl. ....................... 800/298; 435/419; 435/468; 800/284

(58) Field of Search ................................. 435/69.1, 419, 435/468; 536/23.2, 23.6; 800/278, 284, 298

(56) References Cited

U.S. PATENT DOCUMENTS 5,767,365 A * 6/1998 Sonnewald .................. 800/205
5,976,869 A * 11/1999 Sonnewald .................. 435/278

OTHER PUBLICATIONS

Stern M., et al. (1997); "The silence of genes in transgenic plants." Annals of Botany 79:3–12.
Koziel MG, et al. (1996) "Optimizing expression of transgenes with an emphasis on post–transcriptional events." Plant Mol. Biol. 32:393–405.
Smith CTS, et al. (1988) "Andsense RNA Inhibition of polygalacnaronase gene expression in trans genic tomatoes." Nature 334: 724–726.
Worrell AC, et al. (1991); "Expression of maize sucrose phosphate synthese in tomato alters leaf carbohydrate partitioning." The Plant Cell 3:1121–1130.
Sahanoubat M, et al. (1987): Molecular cloning and sequencing of sucrose synthase cDNA from potato (Solanum ruberosum L): Preliminary characteristics of sucrose synthase mRNA distribution.
Carter P. (1986) "Site–directed mutagenesis." Biochem J. 237:1–7.

* cited by examiner

Primary Examiner—Amy J. Nelson
(74) Attorney, Agent, or Firm—Frommer Lawrence & Haug LLP

(57) ABSTRACT

This invention relates to DNA sequences encoding sucrose phosphate synthase which can be integrated into a plant genome and which modify the activity of the sucrose-phosphate-synthase (sps) of the plant. Methods for transforming plant cells and regenerating plants from the cells which exhibit modified sucrose-phosphate-synthase activity are also described.

4 Claims, 3 Drawing Sheets

METHODS FOR THE PREPARATION OF PLANTS WITH CHANGED SUCROSE CONCENTRATION BY TRANSFORMATION WITH A SUCROSE PHOSPHATE SYNTHASE NUCLEIC ACID

CROSS REFERENCE TO RELATED APPLICATIONS

This application is a divisional of application Ser. No. 08/778,656 filed Jan. 3, 1997, now U.S. Pat. No. 5,976,869, which issued on Nov. 2, 1999, which is a divisional of application Ser. No. 08/356,354 filed Dec. 20, 1994, now U.S. Pat. No. 5,767,365, which issued on Jun. 16, 1998, which is a continuation of PCT/EP93/01605 filed Jun. 22, 1993. The disclosure of these applications are hereby incorporated by reference into the present application.

FIELD OF THE INVENTION

The present invention relates to DNA sequences and plasmids, containing these DNA sequences, which by integration into a plant genome, cause the activity of the sucrose-phosphate-synthase (SPS) of the plant to be changed and thus affect the sugar metabolism of the plant. The invention further relates to transgenic plants, in which through introduction of the DNA sequences, changes in the activity of the sucrose-phosphate-synthase are produced.

BACKGROUND OF THE INVENTION

Sucrose is of central importance for the plant and serves many functions. For the long distance transport of photoassimilates and/or energy between various organs in plants, sucrose is almost exclusively used. The sucrose which is transported in a specific heterotrophic organ determines the growth and the development of this organ. Thus it is known, e.g. from EP 442 592, that transgenic plants, in which the transport of the sucrose away from the exporting leaves is inhibited by expression of an apoplastic invertase, shows a strong reduction in the growth of e.g. roots or tubers in the case of potato plants. For tobacco plants, the principal importance of sucrose for the long distance transport of energy carriers within the plant is described in von Schaewen et al, 1990, EMBO J 9: 3033–3044.

While it has been clearly shown that a reduction of the amount of sucrose imported in the heterotrophic organs, such as tubers and seeds, leads to loss of yield, it is not known whether an increase in the amount of sucrose in the photosynthetically active parts of the plant, mainly the leaves, leads to a better supply of heterotrophic organs and thus to an increase in yield.

A second central role for sucrose and/or the hexoses, glucose and fructose which are derived from sucrose, is in the protection of plants against frost damage at low temperatures. Frost damage is one of the main limiting factors in agricultural productivity in the northern hemisphere. Temperatures below freezing lead to the formation of ice crystals. Since the growing ice crystals consist of pure water, water is abstracted from the cells as the temperature falls.

This dehydration has at least two potential damaging results:

a) all dissolved substances within a cell are strongly concentrated and the cell contracts following the loss of water. Highly concentrated salts and organic acids lead to membrane damage;

b) with rehydration from dew, the previously contacted cells reexpand. The cell membrane also expands again. The volume expansion puts a heavy mechanical load on the membrane.

It is thus clear that a freezing/dew cycle can lead to severe membrane damage of the cells and thus to damage to the plant.

It thus appears worth trying to hinder the freezing. One possible strategy is to increase the formation of osmotically active substances in the cytosol of plant cells. This should lead to a lowering of the freezing point. Osmotically active substances include sucrose and/or the two hexoses which are derived from sucrose.

The increased formation of sucrose and/or the two hexoses at low temperatures is desirable in the growing plant. Another situation can exist in the harvested parts of a plant, especially in storage. For example, in potato tubers that are stored at 4–8° C., hexoses (glucose) accumulate. It would appear to be sensible, to see this as the answer to a lowering of the temperature ("cold-sweetening").

The accumulation of sucrose and glucose has in the case of potato tubers economically undesirable results. Increased amounts of reducing sugars, such as glucose, in potatoes which are fried when preparing crisps, chips and the like, leads to an undesirable browning due to the Maillard reaction. Such products with a dark brown color are not generally acceptable to the consumer. Further the cooking strength is strongly dependent on the content of starch and/or its breakdown products which are important in determining the quality characteristics of the potato.

In relation to the economic aspects, sucrose thus possesses three especially important functions:

1 as the transport form for the distant transport of photoassimilates, 2 as an osmotically active substance with the desirable activity of lowering the freezing point in intact, growing plants, and 3 in the undesirable formation of reducing sugars in stored harvested parts of a plant, e.g. the potato tubers, as a result of low temperatures.

The biosynthesis pathways for the formation of sucrose, either from the primary photosynthesis products (in the leaf) or by breakdown of starch (in the storage organs e.g. of potatoes), are known. An enzyme in sucrose metabolism is sucrose-phosphate-synthase (SPS). It forms sucrose-6-phosphate from UDP-glucose and fructose-6-phosphate, which in a second step is converted to sucrose.

The isolation of SPS from maize and the cloning of cDNA from mRNA from maize tissue is known (EP 466 995). In this application, processes for the purification of a protein such as by centrifuging or homogenates, differential precipitation and chromatography are described. A 300 times enrichment of SPS from plant tissue has been described by Salerno and Pontis (Planta 142: 41–48, 1978).

In view of the significance of SPS for carbohydrate metabolism, it is questionable whether plants can tolerate a reduction in SPS activity in all or in certain organs. It is especially not known whether it is possible to produce transgenic plants with a reduced SPS activity. Also the use of SPS for the modification of the functions of sucrose for lowering the freezing point in intact plants and for the formation of reducing sugars in harvested parts is not known.

For the preparation of plants with reduced SPS activity, i.e. plants with changed sucrose concentration, it is necessary to make available an SPS coding region of such plant species, for which processes are described, whereby transgenic plants can be grown in large numbers. In as much as a reduction of SPS activity can be achieved, by selection from a large amount, the possibility exists of obtaining plants with such a phenotype. Further organ specific promoters for gene expression should exist for the plant species, by which the possibility of an organ specific reduction of the SPS activity could be investigated.

A species which fulfils the stated requirements is *Solanum tuberosum*. The genetic modification of *Solanum tuberosum* by gene transfer using Agrobacteria is well described (Fraley et al., 1985, Crit Rev Plant Sci 4: 1–46). Promoters for leaf specific (Stockhaus et al., 1989, Plant Cell 1: 805–813), tuber specific (EP 375 092) and wound inducing (EP 375 091) gene expression are known.

SUMMARY OF THE INVENTION

The present invention now provides DNA sequences with which changes of SPS activity are actually and demonstrably possible and with which the sucrose concentration in the plant can be modified. It is concerned with sequences which include the coding region of sucrose-phosphate-synthase (SPS) from *Solanum tuberosum*.

These DNA sequences can be introduced in plasmids and thereby combined with steering elements for expression in eukaryotic cells. Such steering elements are, on the one hand, transcription promoters and, on the other hand, transcription terminators.

Each plasmid comprises:

a) a suitable promoter that ensures that the coding sequence is read off at the suitable time point and/or in a specified development stage in the transgenic plants or in specified tissues of transgenic plants, b) at least one coding sequence, that
 i) is coupled to the promoter so that RNA can be translated into protein, whereby the protein demonstrates enzymatic activity, that leads to a modification of the sucrose concentration in the plant, or
 ii) is coupled to the promoter so that the non-coding strand is read off, which leads to the formation of a so-called "anti-sense" RNA, which suppresses the formation of the coding protein of an endogenous gene in the plant which is involved in the sucrose biosynthesis, and c) a non-coding termination sequence that contains the signals for the termination and polyadenylation of the transcript.

The present invention further provides plasmids in which include DNA sequences which change the SPS activity in the plant.

The coding sequences named under b) include the SPS sequences with the following nucleotide sequences:

```
SPS 1 sequence (Seq. ID. No. 2):
CTATTCTCTC CCCTCCTTTT TCTCCTCTCT TCAACCCCAA AACTTCCCTT TCAAAGCCTT   60

TGCTTTCCCT TTCTCACTTA CCCAGATCAA CTAAGCCAAT TTGCTGTAGC CTCAGAAAAC  120

AGCATTCCCA GATTGAAAAA GAATCTTTTT CAGTACCCAA AAGTTGGGTT TCTCATGTCC  180

AGCAAGGATT AGCTGCTCTA GCTATTTCTT TAGCCCTTAA TTTTTGTCCA GTTGTGTCTT  240

CTGATTCTGC ATTGGCATCT GAATTTGATG TGTTAAATGA AGGGCCACCA AAGGACTCAT  300

ATGTAGTTGA TGATGCTGGT GTGCTTAGCA GGGTGACAAA GTCTGATTTG AAGGCATTGT  360

TGTCTGATGT GGAGAAGAGA AAAGGCTTCC ACATTAATTT CATCACTGTC CGCAAGCTCA  420

CTAGCAAAGC TGATGCTTTT GAGTATGCTG ACCAAGTTTT GGAGAAGTGG TACCCTAGTG  480

TTGAACAAGG AAATGATAAG GGTATAGTTG TGCTTGTTAC AAGTCAAAAG GAAGGCGCAA  540

TAACCGGTGG CCCTGATTTT GTAAAGGCCG TTGGAGATAC TGTTCTTGAT GCTACCGTCT  600

CAGAGAACCT TCCAGTGTTG GCTACTGAAG AGAAGTACAA TGAAGCAGTT TTCAGCACTG  660

CCACACGTCT TGTTGCAGCC ATTGATGGCC TTCCTGATCC TGGTGGACCC CAACTCAAGG  720

ATAACAAAAG AGAGTCCAAC TTCAAATCCA GAGAGGAAAC TGATGAGAAA AGAGGACAAT  780

TCACACTTGT GGTTGGTGGG CTGTTAGTGA TTGCTTTTGT TGTTCCTATG GCTCAATACT  840

ATGCATATGT TTCAAAGAAG TGAACTGTCT GATTCTGGAA AGTTACATTT TCGTGAGATT  900

TGAGTAAGCA TGTATATTAT CGTGTACAAA ATGGTCCATT CGGAAATGAC TGATTC       956

ATG AGA TAT TTA AAA AGG ATA AAT ATG AAG ATT TGG ACC TCC CCT       1001
Met Arg Tyr Leu Lys Arg Ile Asn Met Lys Ile Trp Thr Ser Pro
1               5                   10                  15

AAC ATA ACG GAT ACT GCC ATT TCT TTT TCA GAG ATG CTG ACG CAA       1046
Asn Ile Thr Asp Thr Ala Ile Ser Phe Ser Glu Met Leu Thr Pro
                20                  25                  30

ATA AGT ACA GAC GGC TTG ATG ACT GAG ATG GGG GAG AGT AGT GGT       1091
Ile Ser Thr Asp Gly Leu Met Thr Glu Met Gly Glu Ser Ser Gly
                35                  40                  45

GCT TAT ATT ATT CGC ATT CCT TTT GGA CCA AGA GAG AAA TAT ATT       1136
Ala Tyr Ile Ile Arg Ile Pro Phe Gly Pro Arg Glu Lys Tyr Ile
```

-continued

```
                 50                      55                       60
CCA AAA GAA CAG CTA TGG CCC TAT ATT CCC GAA TTT GTT GAT GGT            1181
Pro Lys Glu Gln Leu Trp Pro Tyr Ile Pro Glu Phe Val Asp Gly
                 65                      70                      75

GCA CTT AAC CAT ATT ATT CAA ATG TCC AAA GTT CTT GGG GAG CAA            1226
Ala Leu Asn His Ile Ile Gln Met Ser Lys Val Leu Gly Glu Gln
                 80                      85                      90

ATT GGT AGT GGC TAT CCT GTG TGG CCT GTT GCC ATA CAC GGA CAT            1271
Ile Gly Ser Gly Tyr Pro Val Trp Pro Val Ala Ile His Gly His
                 95                     100                     105

TAT GCT GAT GCT GGC GAC TCA GCT GCT CTC CTG TCA GGT GCT TTA            1316
Tyr Ala Asp Ala Gly Asp Ser Ala Ala Leu Leu Ser Gly Ala Leu
                110                     115                     120

AAT GTA CCA ATG CTT TTC ACT GGT CAC TCA CTT GGT AGA GAT AAG            1361
Asn Val Pro Met Leu Phe Thr Gly His Ser Leu Gly Arg Asp Lys
                125                     130                     135

TTG GAG CAA CTG TTG CGA CAA GGT CGT TTG TCA AAG GAT GAA ATA            1406
Leu Glu Gln Leu Leu Arg Gln Gly Arg Leu Ser Lys Asp Glu Ile
                140                     145                     150

AAC TCA ACC TAC AAG ATA ATG CGG AGA ATA GAG GCT GAA GAA TTA            1451
Asn Ser Thr Tyr Lys Ile Met Arg Arg Ile Glu Ala Glu Glu Leu
                155                     160                     165

ACT CTT GAT GCT TCC GAA ATT GTC ATC ACT AGT ACA AGA CAG GAG            1496
Thr Leu Asp Ala Ser Glu Ile Val Ile Thr Ser Thr Arg Gln Glu
                170                     175                     180

ATT GAC GAG CAA TGG CGT TTG TAT GAT GGG TTT GAT CCA ATA TTA            1541
Ile Asp Glu Gln Trp Arg Leu Tyr Asp Gly Phe Asp Pro Ile Leu
                185                     190                     195

GAG CGT AAG TTA CGT GCA AGG ATC AAG CGC AAT GTC AGC TGT TAT            1586
Glu Arg Lys Leu Arg Ala Arg Ile Lys Arg Asn Val Ser Cys Tyr
                200                     205                     210

GGC AGG TTT ATG CCT CGT ATG GCT GTA ATT CCT CCT GGG ATG GAG            1631
Gly Arg Phe Met Pro Arg Met Ala Val Ile Pro Pro Gly Met Glu
                215                     220                     225

TCC CAC CAT ATT GTG CCA CAT GAA GGT GAC ATG GAT GGA GAA ACA            1676
Phe His His Ile Val Pro His Glu Gly Asp Met Asp Gly Glu Thr
                230                     235                     240

GAA GGA AGT GAA GAT GGG AAG ACC CCG GAT CCA CCT ATT TGG GCA            1721
Glu Gly Ser Glu Asp Gly Lys Thr Pro Asp Pro Pro Ile Trp Ala
                245                     250                     255

GAG ATT ATG CGC TTC TTT TCT ATT CCA AGG AAG CCT ATG ATA CTC            1766
Glu Ile Met Arg Phe Phe Ser Ile Pro Arg Lys Pro Met Ile Leu
                260                     265                     270

GCA CTT GCT AGG CCT GAT CCC AAG AAG AAC CTC ACT ACT TTA GTG            1811
Ala Leu Ala Arg Pro Asp Pro Lys Lys Asn Leu Thr Thr Leu Val
                275                     280                     285

AAA GCA TTT GGT GAA TGT CGT CCA TTG AGA GAG CTT GCT AAT CTT            1856
Lys Ala Phe Gly Glu Cys Arg Pro Leu Arg Glu Leu Ala Asn Leu
                290                     295                     300

ACT TTG ATA ATG GGT AAT CGA GAT AAT ATC GAC GAA ATG TCT AGC            1901
Thr Leu Ile Met Gly Asn Arg Asp Asn Ile Asp Glu Met Ser Ser
                305                     310                     315

ACC AAT TCT GCA CTT CTT CTT TCA ATC TTG AAA ATG ATA GAT AAG            1946
Thr Asn Ser Ala Leu Leu Leu Ser Ile Leu Lys Met Ile Asp Lys
                320                     325                     330

TAT GAT CTT TAT GGT CAA GTA GCT TAT CCT AAA CAC CAC AAG CAG            1991
Tyr Asp Leu Tyr Gly Gln Val Ala Tyr Pro Lys His His Lys Gln
                335                     340                     345

TCA GAT GTT CCT GAT ATC TAC CGT CTT GCT GCA AAG ACT AAG GGT            2036
Ser Asp Val Pro Asp Ile Tyr Arg Leu Ala Ala Lys Thr Lys Gly
```

-continued

```
              350                     355                     360
GTT TTT ATT AAT CCA GCT TTT ATT GAG CCT TTT GAA CTG ACT TTG         2081
Val Phe Ile Asn Pro Ala Phe Ile Glu Pro Phe Gly Leu Thr Leu
                365                     370                     375

ATT GAG GCA GCA GCT TAT GGT CTC CCA ATG GTA GCC ACA AAA ATT         2126
Ile Glu Ala Ala Ala Tyr Gly Leu Pro Met Val Ala Thr Lys Asn
                380                     385                     390

GGA GGA CCT GTT GAT ATA CAT AGG GTT CTT GAC AAT GGT CTC TTA         2171
Gly Gly Pro Val Asp Ile His Arg Val Leu Asp Asn Gly Leu Leu
                395                     400                     405

GTG GAT CCC CAT GAT CAG CAG GCA ATT GCT GAT GCT CTT TTG AAG         2216
Val Asp Pro His Asp Gln Gln Ala Ile Ala Asp Ala Leu Leu Lys
                410                     415                     420

TTG GTT GCT GAT AAG CAA CTG TGG GCT AAA TGC AGG GCA AAT GGA         2261
Leu Val Ala Asp Lys Gln Leu Trp Ala Lys Cys Arg Ala Asn Gly
                425                     430                     435

TTA AAA AAT ATC CAC CTT TTC TCA TGG CCC GAG CAC TGT AAA ACT         2306
Leu Lys Asn Ile His Leu Phe Ser Trp Pro Glu His Cys Lys Thr
                440                     445                     450

TAT CTA TCC CGG ATA GCT AGC TGC AAA CCA AGG CAA CCA CGC TGG         2351
Tyr Leu Ser Arg Ile Ala Ser Cys Lys Pro Arg Gln Pro Arg Trp
                455                     460                     465

CTG AGA TCC ATT GAT GAT GAT GAT GAA AAT TCA GAA ACA GAT TCA         2396
Leu Arg Ser Ile Asp Asp Asp Asp Glu Asn Ser Glu Thr Asp Ser
                470                     475                     480

CCT AGT GAT TCC TTG AGA GAT ATT CAT GAT ATA TCT CTG AAT TTG         2441
Pro Ser Asp Ser Leu Arg Asp Ile His Asp Ile Ser Leu Asn Leu
                485                     490                     495

AGA TTT TCA TTA GAT GGG GAA AAG AAT GAC AAT AAA GAA AAT GCT         2486
Arg Phe Ser Leu Asp Gly Glu Lys Asn Asp Asn Lys Glu Asn Ala
                500                     505                     510

GAT AAT ACA TTA GAC CCC GAA GTT CGA AGG AGC AAG TTA GAG AAT         2531
Asp Asn Thr Leu Asp Pro Glu Val Arg Arg Ser Lys Leu Glu Asn
                515                     520                     525

GCT GTT TTG TCC TTA TCT AAG GGT GCA CTG AAG AGC ACA TCA AAA         2576
Ala Val Leu Ser Leu Ser Lys Gly Ala Leu Lys Ser Thr Ser Lys
                530                     535                     540

TCT TGG TCG TCA GAC AAG GCA GAC CAA AAC CCT GGT GCT GGT AAA         2621
Ser Trp Ser Ser Asp Lys Ala Asp Gln Asn Pro Gly Ala Gly Lys
                545                     550                     555

TTC CCA GCG ATT AGG AGG AGG CGA CAT ATT TTT GTT ATT GCA GTG         2666
Phe Pro Ala Ile Arg Arg Arg Arg His Ile Phe Val Ile Ala Val
                560                     560                     565

GAT TGT GAT GCT AGC TCA GGA CTC TCT GGA AGT GTG AAA AAG ATA         2711
Asp Cys Asp Ala Ser Ser Gly Leu Ser Gly Ser Val Lys Lys Ile
                570                     575                     580

TTT GAG GCT GTA GAG AAG GAA AGG GCA GAG GGT TCC ATT GGA TTT         2756
Phe Glu Ala Val Glu Lys Glu Arg Ala Glu Gly Ser Ile Gly Phe
                585                     590                     595

ATC CTG GCT ACA TCT TTC AAT ATA TCA GAA GTA CAG TCT TTC CTG         2801
Ile Leu Ala Thr Ser Phe Asn Ile Ser Glu Val Gln Ser Phe Leu
                600                     605                     610

CTT TCA GAG GGC ATG AAT CCT ACT GAT TTT GAT GCT TAC ATA TGC         2846
Leu Ser Glu Gly Met Asn Pro Thr Asp Phe Asp Ala Tyr Ile Cys
                615                     620                     625

AAT AGT GGT GGT GAT CTT TAT TAT TCG TCC TTC CAT TCT GAG CAA         2891
Asn Ser Gly Gly Asp Leu Tyr Tyr Ser Ser Phe His Ser Glu Gln
                630                     635                     640

AAT CCT TTT GTA GTT GAC TTG TAC TAT CAC TCA CAT ATT GAG TAT         2936
Asn Pro Phe Val Val Asp Leu Tyr Tyr His Ser His Ile Glu Tyr
```

-continued

```
                  645                 650                   655
CGT TGG GGG GGC GAA GGA TTG AGA AAG ACT TTG GTG CGT TGG GCC        2981
Arg Trp Gly Gly Glu Gly Leu Arg Lys Thr Leu Val Arg Trp Ala
                  660                 665                   670

GCC TCT ATC ATT GAT AAG AAT GGT GAA AAT GGA GAT CAC ATT GTT        3026
Ala Ser Ile Ile Asp Lys Asn Gly Glu Asn Gly Asp His Ile Val
                  675                 680                   685

GTT GAG GAT GAA GAC AAT TCA GCT GAC TAC TGC TAT ACT TTC AAA        3071
Val Glu Asp Glu Asp Asn Ser Ala Asp Tyr Cys Tyr Thr Phe Lys
                  690                 695                   700

GTC TGC AAG CCT GGG ACG GTT CCT CCA TCT AAA GAG CTT AGA AAA        3116
Val Cys Lys Pro Gly Thr Val Pro Pro Ser Lys Glu Leu Arg Lys
                  705                 710                   715

GTA ATG CGA ATT CAG GCA CTT CGT TGT CAC GCT GTT TAT TGT CAA        3161
Val Met Arg Ile Gln Ala Leu Arg Cys His Ala Val Tyr Cys Gln
                  720                 725                   730

AAT GGG AGT AGG ATT AAT GTG ATC CCT GTA CTG GCA TCT CGG TCC        3206
Asn Gly Ser Arg Ile Asn Val Ile Pro Val Leu Ala Ser Arg Ser
                  735                 740                   745

CAA GCA CTC AGG TAC TTA TAT CTG CGA TGG GGA ATG GAC TTG TCG        3251
Gln Ala Leu Arg Tyr Leu Tyr Leu Arg Trp Gly Met Asp Leu Ser
                  750                 755                   760

AAG TTG GTG GTT TTC GTC GGA GAA AGT GGT GAT ACC GAT TAT GAA        3296
Lys Leu Val Val Phe Val Gly Glu Ser Gly Asp Thr Asp Tyr Glu
                  765                 770                   775

GGA TTA ATC GGT GGT CTA CGC AAG GCT GTC ATA ATG AAA GGC CTC        3341
Gly Leu Ile Gly Gly Leu Arg Lys Ala Val Ile Met Lys Gly Leu
                  780                 785                   790

TGC ACT AAT GCA AGC AGC TTA ATT CAC GGT AAT AGG AAT TAC CCG        3386
Cys Thr Asn Ala Ser Ser Leu Ile His Gly Asn Arg Asn Tyr Pro
                  795                 800                   805

CTA TCT GAT GTT TTA CCA TTC GAC AGC CCT AAT GTC ATC CAA GCG        3431
Leu Ser Asp Val Leu Pro Phe Asp Ser Pro Asn Val Ile Gln Ala
                  810                 815                   820

GAC GAG GAA TGT AGC AGC ACC GAA ATC CGT TGC TTA CTG GTG AAA        3476
Asp Glu Glu Cys Ser Ser Thr Glu Ile Arg Cys Leu Leu Val Lys
                  825                 830                   835

CTA GCG GTA CTC AAA GGA TAATACCCTT CCCCCTTTGA TTGTCAAAAA           3524
Leu Ala Val Leu Lys Gly
                  840

CCTATATGAG CTATAAGACT ATGCCATGAA AAGAATGGCC ATCCATTTGG CTTGTCTTTT  3584

GAAGCTGTTA ATACTTTTCA ACAGACTACA AAATGAGATG AGTCCTTTGA TCCTCTTTAA  3644

AGGACATAAA AGCTTTATGC AAGAACCAGT GCTGTAAAGT TATAGAATTT CTTTTGCTAT  3704

ATATGACATT CGACAGAACC TGTTCCGGTT CATCGA                            3740

SPS 2 sequence (Seq. ID No. 3 and No.4)

ATTTTTTTCT CTAAGTTCTC TCTCGCTGTC CTTATCATTT CACCACCTCC ATAAATCTAG  60

AAACATCTTT TCTACTCCGT TAATCTCTCT AGCACACGGC GGAGGAGTGC GGCGGAGGAG  120

ATG GCG GGA AAC GAT TGG ATT AAC AGT TAC TTA GAG GCG ATA CTG            165
Met Ala Gly Asn Asp Trp Ile Asn Ser Tyr Leu Glu Ala Ile Leu
1               5                   10                      15

GAT GTT GGA CCA GGG CTA GAT GAT AAG AAG TCA TCG TTG TTG TTG            210
Asp Val Gly Pro Gly Leu Asp Asp Lys Lys Ser Ser Leu Leu Leu
                20                  25                      30

AGA GAA AGA GGG AGG TTT AGT CCG ACG AGG TAC TTT GTT GAG GAA            255
Arg Glu Arg Gly Arg Phe Ser Pro Thr Arg Tyr Phe Val Glu Glu
                35                  40                      45
```

-continued

```
GTT ATT ACT GGA TTC GAT GAG ACT GAT TTG CAT CGT TCG TGG ATC        300
Val Ile Thr Gly Phe Asp Glu Thr Asp Leu His Arg Ser Trp Ile
             50                  55                  60

CGA GCA CAA GCT ACT CGG AGT CCG CAG AGA AGG AAT ACT AGG CTC        345
Arg Ala Gln Ala Thr Arg Ser Pro Gln Arg Arg Asn Thr Arg Leu
             65                  70                  75

GAG AAT ATG TGC TGG AGG ATT TGG AAT TTG GCT CGC CAG AAA AAG        390
Glu Asn Met Cys Trp Arg Ile Trp Asn Leu Ala Arg Gln Lys Lys
             80                  85                  90

CAG CTT GAG GGA GAG CAA GCT CAG TGG ATG GCA AAA CGC CGT CAA        435
Gln Leu Glu Gly Glu Gln Ala Gln Trp Met Ala Lys Arg Arg Gln
             95                 100                 105

GAA CGT GAA AGA GGT CCC AGA GAA GCA GTT GCT GAT ATG TCA GAG        480
Glu Arg Glu Arg Gly Arg Arg Glu Ala Val Ala Asp Met Ser Glu
            110                 115                 120

GAT CTA TCT GAG GGA GAG AAA GGA GAT ATA GTC GCT GAC ATG TCA        525
Asp Leu Ser Glu Gly Glu Lys Gly Asp Ile Val Ala Asp Met Ser
            125                 130                 135

TCT CAT GGT GAA AGT ACC AGA GGC CGA TTG CCT AGA ATC AGT TCT        570
Ser His Gly Glu Ser Thr Arg Gly Arg Leu Pro Arg Ile Ser Ser
            140                 145                 150

GTT GAG ACA ATG GAA GCA TGG GTC AGT CAG CAG AGA GGA AAG AAG        615
Val Glu Thr Met Glu Ala Trp Val Ser Gln Gln Arg Gly Lys Lys
            155                 160                 165

CTT TAT ATC GTG CTT ATA AGT TTA CAT GGT TTA ATT CGG GGT GAG        660
Leu Tyr Ile Val Leu Ile Ser Leu His Gly Leu Ile Arg Gly Glu
            170                 175                 180

AAT ATG GAG CTT GGA CGG GAT TCT GAT ACT GGT GGT CAG GTG AAG        705
Asn Met Glu Leu Gly Arg Asp Ser Asp Thr Gly Gly Gln Val Lys
            185                 190                 195

TAT GTT GTT GAA CTT GCG AGG GGC TTA GGG TCG ATG CCA GGT GTA        750
Tyr Val Val Glu Leu Ala Arg Gly Leu Gly Ser Met Pro Gly Val
            200                 205                 210

TAT CGG GTT GAC TTG CTT ACT AGA CAA GTA TCT TCA CCA GAA GTA        795
Tyr Arg Val Asp Leu Leu Thr Arg Gln Val Ser Ser Pro Glu Val
            215                 220                 225

GAT TGG AGC TAT GGT GAG CCG ACA GAG ATG CTG ACG CCA ATA AGT        840
Asp Trp Ser Tyr Gly Glu Pro Thr Glu Met Leu Thr Pro Ile Ser
            220                 235                 240

ACA GAC GGC TTG ATG ACT GAG ATG GGG GAG AGT AGT GGT GCT TAT        885
Thr Asp Gly Leu Met Thr Glu Met Gly Glu Ser Ser Gly Ala Tyr
            245                 250                 255

ATT ATT CGC ATT CCT TTT GGA CCA AGA GAG AAA TAT ATT CCA AAA        930
Ile Ile Arg Ile Pro Phe Gly Pro Arg Glu Lys Tyr Ile Pro Lys
            260                 265                 270

GAA CAG CTA TGG CCC TAT ATT CCC GAA TTT GTT GAT GGT GCA CTT        975
Glu Gln Leu Trp Pro Tyr Ile Pro Glu Phe Val Asp Gly Ala Leu
            275                 280                 285

AAC CAT ATT ATT CAA ATG TCC AAA GTT CTT GGG GAG CAA ATT GGT       1020
Asn His Ile Ile Gln Met Ser Lys Val Leu Gly Glu Gln Ile Gly
            290                 295                 300

AGT GGC TAT CCT GTG TGG CCT GTT GCC ATA CAC GGA CAT TAT GCT       1065
Ser Gly Tyr Pro Val Trp Pro Val Ala Ile His Gly His Tyr Ala
            305                 310                 315

GAT GCT GGC GAC TCA GCT GCT CTC CTG TCA GGT GCT TTA AAT GTA       1110
Asp Ala Gly Asp Ser Ala Ala Leu Leu Ser Gly Ala Leu Asn Val
            320                 330                 335

CCA ATG CTT TTC ACT GGT CAC TCA CTT GGT AGA GAT AAG TTG GAG       1155
Pro Met Leu Phe Thr Gly His Ser Leu Gly Arg Asp Lys Leu Glu
            340                 345                 350
```

```
                              -continued
CAA CTG TTG GCA CAA GGT CGA AAG TCA AAG GAT GAA ATA AAC TCA          1200
Gln Leu Leu Ala Gln Gly Arg Lys Ser Lys Asp Glu Ile Asn Ser
            355                 360                 365

ACC TAC AAG ATA ATG CGG AGA ATA GAG GCT GAA GAA TTA ACT CTT          1245
Thr Tyr Lys Ile Met Arg Arg Ile Glu Ala Glu Glu Leu Thr Leu
            370                 375                 380

GAT GCT TCC GAA ATT GTC ATC ACT AGT ACA AGA CAG GAG ATT GAC          1290
Asp Ala Ser Glu Ile Val Ile Thr Ser Thr Arg Gln Glu Ile Asp
            385                 390                 395

GAG CAA TGG CGT TTG TAT GAT GGG TTT GAT CCA ATA TTA GAG CGT          1335
Glu Gln Trp Arg Leu Tyr Asp Gly Phe Asp Pro Ile Leu Glu Arg
            400                 405                 410

AAG TTA CGT GCA AGG ATC AAG CGC AAT GTC AGC TGT TAT GGC AGG          1380
Lys Leu Arg Ala Arg Ile Lys Arg Asn Val Ser Cys Tyr Gly Arg
            415                 420                 425

TTT ATG CCT CGT ATG GCT GTA ATT CCT CCT GGG ATG GAG TTC CAC          1425
Phe Met Pro Arg Met Ala Val Ile Pro Pro Gly Met Glu Phe His
            430                 435                 440

CAT ATT GTG CCA CAT GAA GGT GAC ATG GAT GGT GAA ACA GAA GGA          1470
His Ile Val Pro His Glu Gly Asp Met Asp Gly Glu Thr Glu Gly
            445                 450                 455

AGT GAA GAT GGG AAG ACC CCC GAT CCA CCT ATT TGG GCA GAG ATT          1515
Ser Glu Asp Gly Lys Thr Pro Asp Pro Pro Ile Trp Ala Glu Ile
            460                 465                 470

ATG CGC TTC TTT TCT AAT CCA AGG AAG CCT ATG ATA CTC GCA CTT          1560
Met Arg Phe Phe Ser Asn Pro Arg Lys Pro Met Ile Leu Ala Leu
            475                 480                 485

GCT AGG CCT GAT CCC AAG AAG AAC CTC ACT ACT TTA GTG AAA GCA          1605
Ala Arg Pro Asp Pro Lys Lys Asn Leu Thr Thr Leu Val Lys Ala
            490                 495                 500

TTT GGT GAA TGT CGT CCA TTG AGA GAG CTT GCT AAT CTT ACT TTG          1650
Phe Gly Glu Cys Arg Pro Leu Arg Glu Leu Ala Asn Leu Thr Leu
            505                 510                 515

ATA ATG GGT AAT CGA GAT AAT ATC GAC GAA ATG TCT AGC ACC AAT          1695
Ile Met Gly Asn Arg Asp Asn Ile Asp Glu Met Ser Ser Thr Asn
            520                 525                 520

TCT GCA CTT CTT CTT TCA ATC TTG AAA ATG ATA GAT AAG TAT GAT          1740
Ser Ala Leu Leu Leu Ser Ile Leu Lys Met Ile Asp Lys Tyr Asp
            535                 540                 540

CTT TAT GGT CAA GTA GCT TAT CCT AAA CAC CAC AAG CAG TCA GAT          1785
Leu Tyr Gly Gln Val Ala Tyr Pro Lys His His Lys Gln Ser Asp
            545                 550                 555

GTT CCT GAT ATC TAC CGT CTT GCT GCA AAG ACT AAG GGT GTT TTT          1830
Val Pro Asp Ile Tyr Arg Leu Ala Ala Lys Thr Lys Gly Val Phe
            560                 565                 570

ATT AAT CCA GCT TTT ATT GAG CCT TTT GGA CTG ACT TTG ATT GAG          1875
Ile Asn Pro Ala Phe Ile Glu Pro Phe Gly Leu Thr Leu Ile Glu
            575                 580                 585

GCA GCA GCT TAT GGT CTC CCA ATG GTA GCC ACA AAA AAT GGA GGA          1920
Ala Ala Ala Tyr Gly Leu Pro Met Val Ala Thr Lys Asn Gly Gly
            590                 595                 600

CCT GTT GAT ATA CAT AGG GTT CTT GAC AAT GGT CTC TTA GTG GAT          1965
Pro Val Asp Ile His Arg Val Leu Asp Asn Gly Leu Leu Val Asp
            605                 610                 615

CCC CAT GAT CAG CAG GCA ATT GCT GAT GCT CTT TTG AAG TTG GTT          2010
Pro His Asp Gln Gln Ala Ile Ala Asp Ala Leu Leu Lys Leu Val
            620                 625                 630

GCT GAT AAG CAA CTG TGG GCT AAA TGC AGG GCA AAT GGA TTA AAA          2055
Ala Asp Lys Gln Leu Trp Ala Lys Cys Arg Ala Asn Gly Leu Lys
            635                 640                 645
```

-continued

```
AAT ATC CAC CTT TTC TCA TGG CCC GAG CAC TGT AAA ACT TAT CTA        2100
Asn Ile His Leu Phe Ser Trp Pro Glu His Cys Lys Thr Tyr Leu
            650                 655                 660

TCC CGG ATA GCT AGC TGC AAA CCA AGG CAA CCA CGC TGG CTG AGA        2145
Ser Arg Ile Ala Ser Cys Lys Pro Arg Gln Pro Arg Trp Leu Arg
            665                 670                 675

TCC ATT GAT GAT GAT GAT GAA AAT TCA GAA ACA GAT TCA CGT AGT        2190
Ser Ile Asp Asp Asp Asp Glu Asn Ser Glu Thr Asp Ser Pro Ser
            680                 685                 690

GAT TCC TTG AGA GAT ATT CAT GAT ATA TCT CTG AAT TTG AGA TTT        2235
Asp Ser Leu Arg Asp Ile His Asp Ile Ser Leu Asn Leu Arg Phe
            695                 700                 705

TCA TTA GAT GGG GAA AAG AAT GAC AAT AAA GAA AAT GCT GAT AAT        2280
Ser Leu Asp Gly Glu Lys Asn Asp Asn Lys Glu Asn Ala Asp Asn
            710                 715                 720

ACA TTA GAC CCC GAA GTT CGA AGG AGC AAG TTA GAG AAT GCT GTT        2325
Thr Leu Asp Pro Glu Val Arg Arg Ser Lys Leu Glu Asn Ala Val
            725                 730                 735

TTG TCC TTA TCT AAG GGT GCA CTG AAG AGC ACA TCA AAA TCT TGG        2370
Leu Ser Leu Ser Lys Gly Ala Leu Lys Ser Thr Ser Lys Ser Trp
            740                 745                 750

TCG TCA GAC AAG GCA GAC CAA AAC CCT GGT GCT GGT AAA TCC CCA        2415
Ser Ser Asp Lys Ala Asp Gln Asn Pro Gly Ala Gly Lys Phe Pro
            755                 760                 765

GCG ATT AGG AGG AGG CGA CAT ATT TTT GTT ATT GCA GTG GAT TGT        2460
Ala Ile Arg Arg Arg Arg His Ile Phe Val Ile Ala Val Asp Cys
            770                 775                 780

GAT GCT AGC TCA GGA CTC TCT GGA AGT GTG AAA AAG ATA TTT GAG        2505
Asp Ala Ser Ser Gly Leu Ser Gly Ser Val Lys Lys Ile Phe Glu
            785                 790                 795

GCT GTA GAG AAG GAA AGG GCA GAG GGT TCC ATT GGA TTT ATC CTG        2550
Ala Val Glu Lys Glu Arg Ala Glu Gly Ser Ile Gly Phe Ile Leu
            800                 805                 810

GCT ACA TCT TTC AAT ATA TCA GAA GTA CAG TCT TTC CTG CTT TCA        2595
Ala Thr Ser Phe Asn Ile Ser Glu Val Gln Ser Phe Leu Leu Ser
            815                 820                 825

GAG GGC ATG AAT CCT ACT GAT TTT GAT GCT TAC ATA TGC AAT AGT        2640
Glu Gly Met Asn Pro Thr Asp Phe Asp Ala Tyr Ile Cys Asn Ser
            830                 835                 840

GGT GGT GAT CTT TAT TAT TCG TCC TTC CAT TCT GAG CAA AAT CCT        2685
Gly Gly Asp Leu Tyr Tyr Ser Ser Phe His Ser Glu Gln Asn Pro
            845                 850                 855

TTT GTA GTT GAC TTG TAC TAT CAC TCA CAT ATT GAG TAT CGT TGG        2730
Phe Val Val Asp Leu Tyr Tyr His Ser His Ile Glu Tyr Arg Trp
            860                 865                 870

GGG GGC GAA GGA TTG AGA AAG ACT TTG GTG CGT TGG GCC GCC TCT        2775
Gly Gly Glu Gly Leu Arg Lys Thr Leu Val Arg Trp Ala Ala Ser
            875                 880                 885

ATC ATT GAT AAG AAT GGT GAA AAT GGA GAT CAC ATT GTT GTT GAG        2820
Ile Ile Asp Lys Asn Gly Glu Asn Gly Asp His Ile Val Val Glu
            890                 895                 900

GAT GAA GAC AAT TCA GCT GAC TAC TGC TAT ACT TTC AAA GTG TGC        2865
Asp Glu Asp Asn Ser Ala Asp Tyr Cys Tyr Thr Phe Lys Val Cys
            905                 910                 915

AAG CCT GGG AGG GTT GCT CCA TGT AAA GAG GTT AGA AAA GTA ATG        2910
Lys Pro Gly Arg Val Ala Pro Cys Lys Glu Val Arg Lys Val Met
            920                 925                 930

CGA ATT CAG GCA GTT CGT TGT CAC GCT GTT TAT TGT CAA AAT GGG        2955
Arg Ile Gln Ala Leu Arg Cys His Ala Val Tyr Cys Gln Asn Gly
            935                 940                 945
```

```
                                                -continued
AGT AGG ATT AAT GTG ATC CCT GTA CTG GCA TCT CGG TCC CAA GCA         3000
Ser Arg Ile Asn Val Ile Pro Val Leu Ala Ser Arg Ser Gln Ala
                950                 955                 960

CTC AGG TAC TTA TAT CTG CGA TGG GGA ATG GAC TTG TCG AAG TTG         3045
Leu Arg Tyr Leu Tyr Leu Arg Trp Gly Met Asp Leu Ser Lys Leu
                965                 970                 975

GTG GTT TTC GTC GGA GAA AGT GGT GAT ACC GAT TAT GAA GGA TTA         3090
Val Val Phe Val Gly Glu Ser Gly Asp Thr Asp Tyr Glu Gly Leu
                980                 985                 990

ATG GGT GGT CTA CGC AAG GCT GTC ATA ATG AAA GGC CTC TGC ACT         3135
Ile Gly Gly Leu Arg Lys Ala Val Ile Met Lys Gly Leu Cys Thr
                995                 1000                1005

AAT GCA AGC AGC TTA ATT CAC GGT AAT AGG AAT TAC CCG CTA TCT         3180
Asn Ala Ser Ser Leu Ile His Gly Asn Arg Asn Tyr Pro Leu Ser
                1010                1015                1020

GAT GTT TTA CCA TTC GAC AGC CCT AAT GTC ATC CAA GCG GAC GAG         3225
Asp Val Leu Pro Phe Asp Ser Pro Asn Val Ile Gln Ala Asp Glu
                1025                1030                1035

GAA TGT AGC AGC ACC GAA ATC CGT TGC TTA CTG GAG AAA CTA GCG         3270
Glu Cys Ser Ser Thr Glu Ile Arg Cys Leu Leu Glu Lys Leu Ala
                1040                1045                1050

GTA CTC AAA GGA TAA TACCCTTCCC CCTTTGATTG TCAAAAACCT                3315
Val Leu Lys Gly End
            1054

ATATGAGCTA TAAGACTATG GCATGAAAAG AATGGCCATC CATTTGGCTT GTCTTTTGAA   3375

GCTGTTAATA CTTTTCAACA GACTACAAAA TGAGATGAGT CCTTTGATCC TCTTTAAAGG   3435

ACATAAAAGC TTTATGCAAG AACCAGTGCT GTAAAGTTAT AGAATTTCTT TTGCTATATA   3495

TGACATTCGA CAGAACCAGT TCCGGTTCAT CGAGAAAAAG AAATAAATTT CAACTTATAA   3555

ACATGCCTGA TCATGTAAAT TATCATATAC ATCCATCGGA AGGCATTATC GATGGGTTAT   3615

CAGATTTTTT                                                          3625

SPS 3 sequence (Seq. ID No.5 and No.6)

ATTTTTT TCTCTAAATT CTCTCTCACT GTCCTTATCA TTTCACCACC TCCATAAATC  57

TAGAAACATC TTTTCTATTC CGTTAATCTC TGTAGCACAC GGCGGAGTGC GGCGGAGGAG    117

ATG GCG GGA AAC GAC TGG ATT AAC AGT TAG TTA GAG GCG ATA CTG          162
Met Ala Gly Asn Asp Trp Ile Asn Ser Tyr Leu Glu Ala Ile Leu
1                   5                   10                  15

GAT GTA GGA CCA GGG CTA GAT GAT AAG AAA TCA TCG TTG TTG TTG          207
Asp Val Gly Pro Gly Leu Asp Asp Lys Lys Ser Ser Leu Leu Leu
                    20                  25                  30

AGA GAA AGA GGG AGG TTT AGT CCG ACG AGG TAC TTT GTT GAG GAA          252
Arg Glu Arg Gly Arg Phe Ser Pro Thr Arg Tyr The Val Glu Glu
                    25                  40                  45

GTT ATT ACT GGA TTC GAT GAG ACT GAT TTG CAT CGC TCG TGG ATC          297
Val Ile Thr Gly Phe Asp Glu Thr Asp Leu His Arg Ser Trp Ile
                    50                  55                  60

CGA GCA CAA GCT ACT CGG AGT CCG CAG GAG AGG AAT ACT AGG CTC          342
Arg Ala Gln Ala Thr Arg Ser Pro Gln Glu Arg Asn Thr Arg Leu
                    65                  70                  75

GAG AAT ATG TGC TGG AGG ATT TGG AAT TTG GCT CGC CAG AAA AAG          387
Glu Asn Met Cys Trp Arg Ile Trp Asn Leu Ala Arg Gln Lys Lys
                    80                  85                  90

CAG CTT GAG GGA GAG CAA GCT CAG TGG ATG GCA AAA CGC CGT CAA          432
Gln Leu Glu Gly Glu Gln Ala Gln Trp Met Ala Lys Arg Arg Gln
                    95                  100                 105

GAA CGT GAG AGA GGT CGC AGA GAA GCA GTT GCT GAT ATG TCA GAG          477
```

-continued

```
              Glu Arg Glu Arg Gly Arg Arg Glu Ala Val Ala Asp Met Ser Glu
                              110                 115                 120

GAT CTA TCT GAG GGA GAG AAA GGA GAT ATA GTC GCT GAC ATG TCA              522
Asp Leu Ser Glu Gly Glu Lys Gly Asp Ile Val Ala Asp Met Ser
                125                 130                 135

TCT CAT GGT GAA AGT ACC AGA GGC CGA TTG CCT AGA ATC AGT TCT              567
Ser His Gly Glu Ser Thr Arg Gly Arg Leu Pro Arg Ile Ser Ser
                140                 145                 150

GTT GAG ACA ATG GAA GCA TGG GTC AGT CAG CAG AGA GGA AAG AAG              612
Val Glu Thr Met Glu Ala Trp Val Ser Gln Gln Arg Gly Lys Lys
                155                 160                 165

CTT TAT ATC GTG CTT ATA AGT TTA CAT GGT TTA ATT CGG GGT GAG              657
Leu Tyr Ile Val Leu Ile Ser Leu His Gly Leu Ile Arg Gly Glu
                170                 175                 180

AAT ATG GAG CTT GGA CGG GAT TCT GAT ACT GGT GGT CAG GTG AAG              702
Asn Met Glu Leu Gly Arg Asp Ser Asp Thr Gly Gly Gln Val Lys
                185                 190                 195

TAT GTA GTT GGA GCA ACT GTT GCA CAA GGT CGT TTG TCA AAG GAT              747
Tyr Val Val Gly Ala Thr Val Ala Gln Gly Arg Leu Ser Lys Asp
                200                 205                 210

GAA ATA AAC TCA ACC TAC AAG ATA ATG CGG AGA ATA GAG GGT GAA              792
Glu Ile Asn Ser Thr Tyr Lys Ile Met Arg Arg Ile Glu Ala Glu
                215                 220                 225

GAA TTA ACT CTT GAT GCT TCC GAA ATT GTC ATC ACT AGT ACA AGA              837
Glu Leu Thr Leu Asp Ala Ser Glu Ile Val Ile Thr Ser Thr Arg
                230                 235                 240

CAG GAG ATT GAC GAG CAA TGG CGT TTG TAT GAT GGG TTT GAT CCA              882
Gln Glu Ile Asp Glu Gln Trp Arg Leu Tyr Asp Gly Phe Asp Pro
                245                 250                 255

ATA TTA GAG CGT AAG TTA CGT GCA AGG ATC AAG CGC AAT GTC AGC              927
Ile Leu Glu Arg Lys Leu Arg Ala Arg Ile Lys Arg Asn Val Ser
                260                 265                 270

TGT TAT GGC AGG TTT ATG CCT CGT ATG GCT GTA ATT CCT CCT GGG              972
Cys Tyr Gly Arg Phe Met Pro Arg Met Ala Val Ile Pro Pro Gly
                275                 280                 285

ATG GAG TTC CAC CAT ATT GTG CCA CAT GAA GGT GAC ATG GAT GGT             1017
Met Glu Phe His His Ile Val Pro His Glu Gly Asp Met Asp Gly
                290                 295                 300

GAA ACA GAA GGA AGT GAA GAT GGA AAG ACC CCG GAT CCA CCT ATT             1062
Glu Thr Glu Gly Ser Glu Asp Gly Lys Thr Pro Asp Pro Pro Ile
                305                 310                 315

TGG GCA GAG ATT ATG CGC TTC TTT TCT AAT CCA AGG AAG CCT ATG             1107
Trp Ala Glu Ile Met Arg Phe Phe Ser Asn Pro Arg Lys Pro Met
                320                 330                 335

ATA CTC GCA CTT GCT AGG CCT GAT CCC AAG AAG AAC CTC ACT ACT             1152
Ile Leu Ala Leu Ala Arg Pro Asp Pro Lys Lys Asn Leu Thr Thr
                340                 345                 350

TTA GTG AAA GCA TTT GGT GAA TGT CGT CCA TTG AGA GAC CTT GCT             1197
Leu Val Lys Ala Phe Gly Glu Cys Arg Pro Leu Arg Asp Leu Ala
                355                 360                 365

AAT CTT ACT TTG ATA ATG GGT AAT CGA GAT AAT ATC GAC GAA ATG             1242
Asn Leu Thr Leu Ile Met Gly Asn Arg Asp Asn Ile Asp Glu Met
                370                 375                 380

TCT AGC ACC AAT TCT GCA CTT CTT CTT TCA ATC TTC AAG ATG ATA             1287
Ser Ser Thr Asn Ser Ala Leu Leu Leu Ser Ile Leu Lys Met Ile
                385                 390                 395

GAT AAG TAT GAT CTT TAT GGT CTA GTA GCT TAT CCT AAA CAC CAC             1332
Asp Lys Tyr Asp Leu Tyr Gly Leu Val Ala Tyr Pro Lys His His
                400                 405                 410

AAG CAG TCA GAT GTT CCT GAT ATC TAC CGT CTT GCT GCA AAG ACT             1377
```

-continued

```
Lys Gln Ser Asp Val Pro Asp Ile Tyr Arg Leu Ala Ala Lys Thr
            415                 420                 425

AAG GGT GTT TTT ATT AAT CCA GCT TTT ATT GAG CCT TTT GGA CTG      1422
Lys Gly Val Phe Ile Asn Pro Ala Phe Ile Glu Pro Phe Gly Leu
            430                 435                 440

ACT TTG ATT GAG GCA GCA GCT TAT GGT CTC CCA ATG GTA GCC ACA      1467
Thr Leu Ile Glu Ala Ala Ala Tyr Gly Leu Pro Met Val Ala Thr
            445                 450                 455

AAA AAT GGA GGA CCT GTT CAT ATA GAT AGG GTT CTT GAC AAT GGT      1512
Lys Asn Gly Gly Pro Val Asp Ile His Arg Val Leu Asp Asn Gly
            460                 465                 470

CTC TTA GTG GAT CCC CAT GAT CAG CAG GCA ATT GCT GAT GCT CTT      1557
Leu Leu Val Asp Pro His Asp Gln Gln Ala Ile Ala Asp Ala Leu
            475                 480                 485

TTG AAG TTG GTT GCT GAT AAG CAA CTG TGG GCT AAA TGC AGG GCA      1602
Leu Lys Leu Val Ala Asp Lys Gln Leu Trp Ala Lys Cys Arg Ala
            490                 495                 500

AAT GGA TTA AAA AAT ATG CAC CTT TTC TCA TGG CCC GAG CAC TGT      1647
Asn Gly Leu Lys Asn Met His Leu Phe Ser Trp Pro Glu His Cys
            505                 510                 515

AAA ACT TAT CTA TCC CGG ATA GCT AGC TGC AAA CCG AGG CAA CAT      1692
Lys Thr Tyr Leu Ser Arg Ile Ala Ser Cys Lys Pro Arg Gln His
            520                 525                 530

TCC TTG AGA GAT ATT CAT GAT ATA TCT CTG AAT TTG AGA TTT TCA      1737
Ser Leu Arg Asp Ile His Asp Ile Ser Leu Asn Leu Arg Phe Ser
            535                 540                 540

TTA GAT GGG GAA AAG AAT GAC AAT AAA GAA AAT GCT GAT AAT ACA      1782
Leu Asp Gly Glu Lys Asn Asp Asn Lys Glu Asn Ala Asp Asn Thr
            545                 550                 555

TTA GAC CCC GAA GTT CGA AGG AGC AAG TTA GAG AAT GCT GTT TTG      1827
Leu Asp Pro Glu Val Arg Arg Ser Lys Leu Glu Asn Ala Val Leu
            560                 565                 570

TCC TTA TCT AAG GGT GCA CTG AAG AGC ACA TCA AAA TCT TGG TCG      1872
Ser Leu Ser Lys Gly Ala Leu Lys Ser Thr Ser Lys Ser Trp Ser
            575                 580                 585

TCA GAC AAG GCA GAC CAA AAT CCT GGT GCT GGT AAA TTC CCA GCG      1917
Ser Asp Lys Ala Asp Gln Asn Pro Gly Ala Gly Lys Phe Pro Ala
            590                 595                 600

ATT AGG AGG AGG CGA CAT ATT TTT GTT ATT GCA GTG GAT TGT GAT      1962
Ile Arg Arg Arg Arg His Ile Phe Val Ile Ala Val Asp Cys Asp
            605                 610                 615

GCT AGC TCA GGA CTC TCT GGA AGT ATG AAA AAG ATA TTT GAG GCT      2007
Ala Ser Ser Gly Leu Ser Gly Ser Met Lys Lys Ile Phe Glu Ala
            620                 625                 630

GTA GAG AAG GAA AGG GCA GAG GGT TCC ATT GGA TTT ATC CTT GCT      2052
Val Glu Lys Glu Arg Ala Glu Gly Ser Ile Gly Phe Ile Leu Ala
            635                 640                 645

ACA TCT TTC AAT ATA TCA GAA GTA CAG TCT TTC CTG CTT TCA GAG      2097
Thr Ser Phe Asn Ile Ser Glu Val Gln Ser Phe Leu Leu Ser Glu
            650                 655                 660

GGC ATG AAT CCT ACT GAG CAA AAT CCT TTT GTA GTT GAC TTG TAC      2142
Gly Met Asn Pro Thr Glu Gln Asn Pro Phe Val Val Asp Leu Tyr
            665                 670                 675

TAT CAC TCA CAT ATT GAG TAT CGT TGG GGG GGC GAA GGG TTG AGA      2187
Tyr His Ser His Ile Glu Tyr Arg Trp Gly Gly Glu Gly Leu Arg
            680                 685                 690

AAG ACT TTG GTG CGT TGG GCC GCC TCT ATC ATT GAT AAG AAT GGT      2232
Lys Thr Leu Val Arg Trp Ala Ala Ser Ile Ile Asp Lys Asn Gly
            695                 700                 705

GAA AAT GGA GAT CAC ATT GTT GTT GAG GAT GAA GAC AAT TCA GCT      2277
```

```
                             -continued
Glu Asn Gly Asp His Ile Val Val Glu Asp Glu Asp Asn Ser Ala
                705             710                 715                 720

GAC TAC TGC TAT ACA TTC AAA GTT TGC AAG CCT GGG ACG GTT CCT          2322
Asp Tyr Cys Tyr Thr Phe Lys Val Cys Lys Pro Gly Thr Val Pro
                725                 730                 725

CCA TCT AAA GAA CTT AGA AAA GTA ATG CGA ATT CAG GCA CTT CGT          2367
Pro Ser Lys Glu Leu Arg Lys Val Met Arg Ile Gln Ala Leu Arg
                740                 745                 750

TGT CAC GCT GTT TAT TGT CAA AAT GGG AGT AGG ATT AAT GTG ATC          2412
Cys His Ala Val Tyr Cys Gln Asn Gly Ser Arg Ile Asn Val Ile
                755                 760                 765

CCT GTA CTG GCA TCT CGG TCC CAA GCA CTC AGG TAC TTA TAT CTG          2457
Pro Val Leu Ala Ser Arg Ser Gln Ala Leu Arg Tyr Leu Tyr Leu
                770                 775                 780

CGA TGG GGA ATG GTC CCT GTA CTG GCA TCT CGG TCC CAA GCA CTC          2502
Arg Trp Gly Met Val Pro Val Leu Ala Ser Arg Ser Gln Ala Leu
                785                 790                 795

AGG TAC TTA TAT CTG CGA TGG GGA ATG GTC CCT GTA CTG GCA TCT          2547
Arg Tyr Leu Tyr Leu Arg Trp Gly Met Val Pro Val Leu Ala Ser
                800                 805                 810

CGG TCC CAA GCA CTC AGG TAC TTA TAT GTG CGA TGG GGA ATG GAC          2592
Arg Ser Gln Ala Leu Arg Tyr Leu Tyr Leu Arg Trp Gly Met Asp
                815                 820                 825

TTG TCG AAG TTG GTG GTT TTC GTC GGA GAA AGT GGT GAT ACC GAT          2637
Leu Ser Lys Leu Val Val Phe Val Gly Glu Ser Gly Asp Thr Asp
                830                 835                 840

TAT GAA GGA TTG ATC GGT GGT CTA CGC AAG GCT GTC ATA ATG AAA          2682
Tyr Glu Gly Leu Ile Gly Gly Leu Arg Lys Ala Val Ile Met Lys
                845                 850                 855

GGA CTC TGC ACT AAT GCA AGC AGC TTA ATT CAC GGT AAT AGG AAT          2727
Gly Leu Cys Thr Asn Ala Ser Ser Leu Ile His Gly Asn Arg Asn
                860                 865                 870

TAC CCG CTA TCT GAT GTT TTA CCA TTC GAG AGC CCT AAT GTC ATC          2772
Tyr Pro Leu Ser Asp Val Leu Pro Phe Glu Ser Pro Asn Val Ile
                875                 880                 885

CAA GCG GAT GAG GAA TGT AGC AGC ACC GGA ATC CGT TCC TTA CTG          2817
Gln Ala Asp Glu Glu Cys Ser Ser Thr Gly Ile Arg Ser Leu Leu
                905                 910                 915

GAG AAA CTA GCG GTA CTC AAA GGA TAA TACCCTTCCC CCTTTGATTG            2864
Glu Lys Leu Ala Val Leu Lys Gly End
                920

TCAAAAACCT ATATGAGCTA AGATTATGCC ATGAAAAGAA TGGCCATCCA TTTGGCTTGT   2924

CTTTTG                                                               2930
```

All sequences are cDNA sequences and stem from a cDNA library of leaf tissue. The expression gene is the same in various plant tissues. As a promoter, there can generally be used any promoter which is active in plants. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters are e.g. the promoter of the 355 RNA of the cauliflower mosaic virus, the patatin promoter B33 (Rocha-Sosa et al. (1989) EMBO J 8: 23–29) or a promoter that ensures expression only in photosynthetically active tissues. Other promoters can be used which ensure expression only in specified organs, such as the root, tuber, seed, stem or specified cell types such as mesophyllic, epidermal or transport cells. For hindering cold sweetening, suitable promoters are those which ensure an activation of the transcription is stored in harvested parts of the plants. For this, there can be considered cold induced promoters or such promoters that become active during the transition of the tuber from the phase where it stores material to the phase where it gives up material.

DETAILED DESCRIPTION OF THE INVENTION

Figure 1:
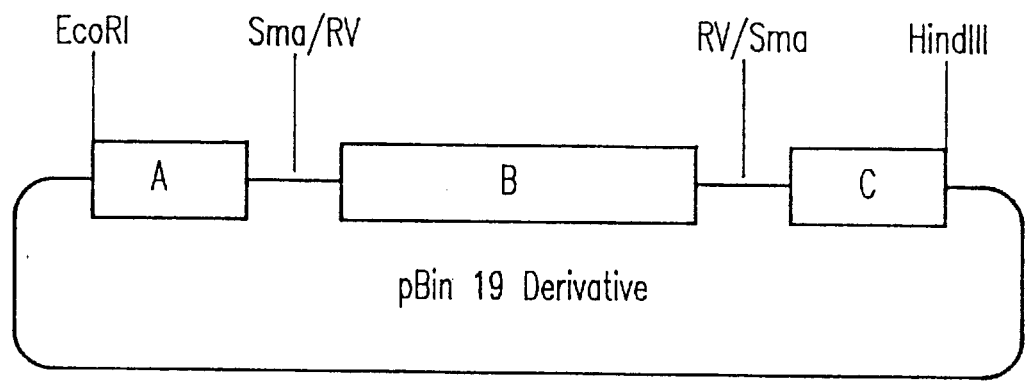
FIG. 1 provides the structure of the 35S-anti-pot-SPS gene.

The coding sequence contains the information for the formation of an mRNA for the sucrose-phosphate-synthase (SPS) or for the formation of an anti-sense RNA for the SPS. Whether the translatable MRNA or an anti-sense RNA is formed depends on the orientation of the coding sequence in relation to the promoter. If the 3' end of the coding sequence is fused to the 3' end of the promoter, an anti-sense RNA results, while the fusion of the 5' end of the coding sequence to the 3' end of the promoter promoter, a translatable RNA results. This latter leads to an increase of the SPS activity in the cell, while the first leads to a reduction of the SPS activity in the cell. Such a reduction of SPS activity is especially significant in view of the undesirable formation of sucrose and/or reducing sugars as a result of cold storage of harvested organs.

The coding sequence for SPS can be one of the three described above or one that is derived by modifications of the sequences described above. A derivation can be carried out, e.g. by current methods of mutagenesis and/or recombination. In particular, changes of SPS sequences that lead to a neutralisation of the plant's own regulation mechanism are contemplated.

The DNA sequences of the invention can also be used for the preparation of derivatives whose gene products are not subjected to the plant's own activity regulation during a phosphorylation reaction.

Further, the sequences can also be used for the preparation of derivatives by targeted and non-targeted mutagenesis.

The invention relates further to derivatives of the DNA sequences of the invention that are-obtained by exchange of single bases or by deletion or insertion of base sequences and which code for proteins with a comparable activity to sucrose-phosphate-synthase.

The 5' untranslated area of the sequence Seq. ID No 1, is not part of SPS, but is shown as a cloning artefact. The methionine start codon of the coding region lies in a region in which there is no homology of the amino acid sequence to the other SPS sequences. Since this sequence does not also fully coincide in the homologous region with one of the other sequences, it is recognisable that the sequence Seq. ID No 1 is not a derivative of the sequences Seq. ID No 3 and Seq. ID No 5.

The termination sequence provides the correct finishing of the transcription and the attachment of a polyadenyl group to the RNA. This polyadenyl group has an important function in the stabilisation of RNA molecules in the cells. With suitable plasmids which contain the DNA sequences of the invention, plants can be transformed with the object of raising and/or reducing the SPS activity and/or modifying the sucrose concentration.

Plasmids that can be used include e.g. p35S-anti-pot-SPS (DSM 7125) and pB33-anti-pot-SPS (DSM 7124). With the gene 35S-anti-pot-SPS, located on the plasmid p355-anti-pot-SPS, the concentration of the mRNA for the SPS protein and the enzymatic activity, for example, can be reduced. With the gene B335-anti-pot-SPS, located on the plasmid pB33-anti-pot-SPS, the concentration of the mRNA for the SPS protein and the enzymatic activity, specifically for potato tubers for example, can be reduced. In a similar way to the SPS sequence (Seq. ID No. 1) located on this plasmid, other SPS sequences, e.g. the sequences Seq. ID No. 3 and Seq. ID No. 5 also be cloned in suitable vectors and for the same purpose.

In the plant, the SPS is subjected to an activity control by phosphorylation. This allows the plant to regulate the activity of the enzyme within a fixed frame independent of the amount of the SPS protein. If one of the changes occurring outside the activity of the SPS is to be achieved, it is necessary to evade the plant's own regulation mechanism. Therefore changing the phosphorylation possibilities is an important target for influencing the SPS activity and thus the sucrose content of the plant.

It is not known in which position in the SPS protein target directed changes of the coding regions can be achieved which serve the purpose of introducing in the plant SPS activity which is not subject to any of the plant's own controls.

The DNA sequence described here, which contains the coding region for SPS from *Solanum tuberosum*, allows the identification of the sites of protein phosphorylation of the SPS. By using standard methods (Sambrook, J., Fritsch, E. F., Maniatis, T. (1989) Molecular Cloning: A laboratory Manual, 2nd. Edn., Cold Spring Harbor Laboratory Press, NY, USA), a localisation of the phosphorylation positions of SPS is possible using the DNA sequences of the invention. These being known, by use of the plasmids with the SPS sequence, a target directed mutagenesis (Sambrook et al, 1989) of the coding region of SPS and/or a non-target directed mutagenesis (Sambrook et al, 1989) and subsequent probing of the desired mutations of the coding region of the SPS can be undertaken. Derivatives of the coding region can be prepared with the help of this plasmid, whose derived proteins are not subjected to the plants own regulation mechanisms.

Since the SPS enzyme is regulated by phosphorylation in all tested species, except maize, one can refer to sequence comparisons to identify possible phosphorylation sites. The criterium for this is that a serine residue appears in an acidic medium in the regulated SPS protein, but not however with maize. There are 12 such serine residues in the sequences, Seq. ID No. 3 and Seq ID No. 5. In the sequence Seq ID No. 1, the first of the 12 serine residues is missing, since the coding region begins just later. The sequence, Seq. ID No. 1 is thus especially suitable for the production of SPS activity in plants that is not liable to endogenous activity regulation.

For the introduction of the SPS sequence in higher plants, a large number of cloning vectors are available which contain a replication signal for *E. coli* and a marker, which allows for the selection of the transformed cells. Examples of vectors are pBR 322, pUC-series, M13 mp-series, PACYC 184; EMBL 3 etc. According to the introduction method of the desired gene in the plant, other DNA sequences may be suitable. Should the Ti- or Ri-plasmid be used, e.g. for the transformation of the plant cell, then at least the right boundary, often however both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offset-drukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium which contains antibiotics or biocides for selection. The resulting plants can then betested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al.(1986) Plant Cell Reports 5: 81–84). These plants can be grown normally and crossed with plants, that possess the same transformed genes or different genes. The resulting hybrid individuals have the corresponding phenotypical properties.

Deposits

The following plasmids were deposited at the Deutschen Sammlung von Mikroorganismen (DSM) in Braunschweig, Germany on the 12.06.1992 (deposit number):

Plasmid p35S-anti-pot-SPS (DSM 7125) Plasmid pB33-anti-pot-SPS (DSM 7124)

DETAILED DESCRIPTIONS OF THE DRAWINGS

Figure 2:
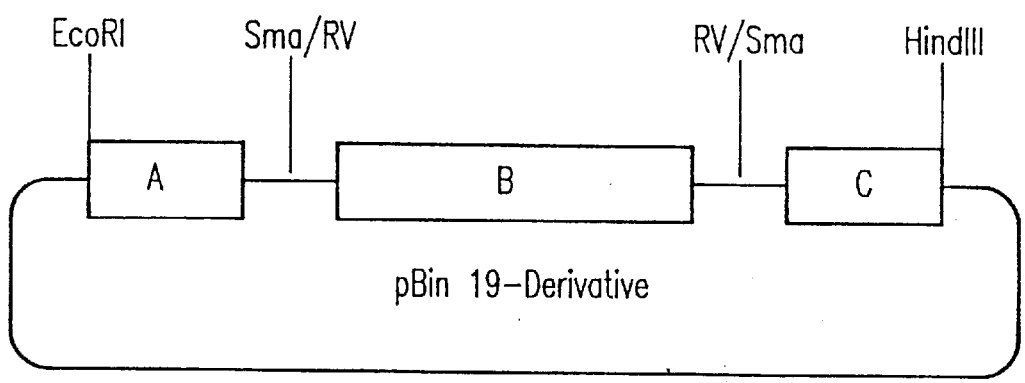
FIG. 2 provides the structure of the B33-anti-pot-SPS gene.
Figure 3:
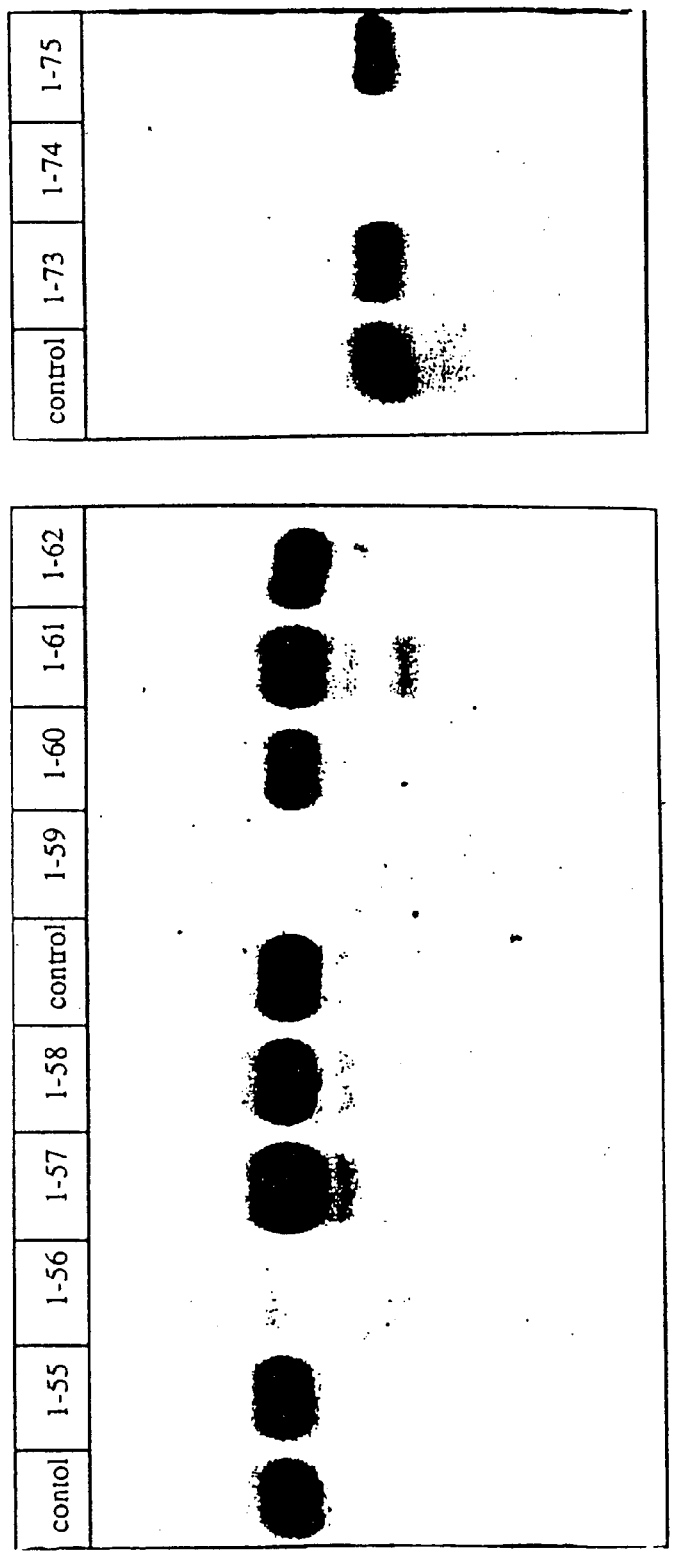
FIG. 3 provides an analysis of plants transformed with a plasmid which included the 35S-anti-pot-SPS gene.

FIG. 1: Structure of the 35S-anti-pot-SPS gene
A=Fragment A: CaMV 35S promoter, nt 6909–7437 (Franck et al.,1980, Cell 21: 285–294)
B=Fragment B: sucrose phosphate synthase, EcORV Fragment (nt 1 bis 2011), ca. 2000 bp, orientation: anti-sense
C=Fragment C: nt 11748–11939 of the T-DNA of the Ti-plasmid pTiACH5; Gielen et al., 1984, EMBO J 3: 835–846)
FIG. 2: Structure of the B33-anti-pot-SPS gene
A=Fragment A: B33 promoter of the patatin gene from S. tuberosum, (Rocha-Sosa et al., 1989, EMBO J 8: 23–29), ca 530 bp
B=Fragment B: sucrose phosphate synthase (s. FIG. 2), EcoRV fragment (nt 2011 bis 1), ca. 2000 bp, orientation: anti-sense
C=Fragment C: nt 11748–11939 of T-DNA of the Ti-plasmid pTiACH5 (Gielen et al., 1984, EMBO J 3: 835–846)
FIG. 3: shows the results of the transformation of transgenic potato plants.
Control=wild type plants
1–75=individual transgenic plants
FIG. 4: shows the results of the transformation of potato plants
Control=wild type plants
3–20=individual transgenic plants In order to understand the examples forming the basis of this invention all the processes necessary for these tests and which are known per se will first of all be listed:

1. Cloning Process

The vectors pUC 18/19 and M13mp10 series (Yanisch-Perron et al. (1985) Gene 33: 103–119), as well as the vector EMBL 3 (Frischauf et al. (1983) J Mol Biol 170: 827–842) were used for cloning.

For the plant transformations, the gene constructs were cloned in the binary vector BIN 19 (Bevan (1984) Nucl. Acids Res 12: 8711–8720)

2. Bacterial Strains

The E. coli strain BMH71-18 (Messing et al., Proc. Natl. Acad. Sci. USA (1977), 24, 6342–6346) or TB1 was used for the pUC and M13 mP vectors.

For the vector BIN19, only the E. coli strain TB1 was used. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F' (traD36, proAB, lacI, lacZΔM15), Δ (lac, pro), SupE, this, recA, Sr1::Tn10 (TcR).

The transformation of the plasmids into the potato plants was carried out using Agrobacterium tumefaciens strain LBA4404 (Bevan, (1984), Nucl. Acids Res. 12, 8711–8720).

3. Transformation of Agrobacterium tumefaciens

In the case of BIN19 derivatives, the insertion of the DNA into the Agrobacterium was effected by direct transformation in accordance with the method of Holsters et al., (1978) (Mol Gene Genet 163: 181–187). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Plant Transformation

Ten small leaves, wounded with a scalpel, of a sterile potato culture were placed in 10 ml of MS medium with 2% sucrose containing 30–50 μl of an Agrobacterium tumefaciens overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

5. SPS Activity Test

The SPS activity was determined according to the method of Siegel and Stitt (1990, Plant Science 66: 205–210) in a two stage analysis. To 180 μl of a solution of 50 mM HEPES/KOH (pH 7.4), 5 mM magnesium chloride, 5 mM fructose-6-phosphate, 25 mM glucose-6-phosphate and 6 mM uridine-5'-diphosphoglucose 20 μl of probe was added and incubated for 10 minutes at 25° C. It was heated for 3 minutes at 95°C., to complete the reaction. After centrifuging, the supernatant was spectroscopically analysed for the liberation of uridine-5'-diphosphate, whereby a pyruvate-kinase coupling enzyme reaction was used. Preparations without hexose phosphate, as well as the measurement of the recovery of added uridine-5'-diphosphate act as controls.

EXAMPLES

Example 1

Clonina of genes of the sucrose-phosphate-synthase from potato

Poly-A+ RNA was isolated from large leaves of spinach plants as well as potato plants grown in the greenhouse.

Resulting from the poly-A+ RNA, a CDNA library in the expression vector Lambda Zap II was laid out. 100,000 plaques of both libraries were separated from spinach using a rabbit antiserum directed against pure SPS protein in relation to immunologically cross reacting protein. (Sonnewald et al., 1992, in press). From the potato library, positively reacting clones were obtained. These clones were further purified by standard methods and, by in vivo excision, plasmids were obtained which carried a double stranded cDNA as an insertion. After testing the size of the insertions, individual clones were analysed by determining the primary sequence.

Example 2

Determination of the Nucleotide Seauence of the SPS from Potato Codina cDNA Molecules and Derivation of the Corresponding Amino acid Sequences The nucleotide sequences of the insertions obtained from Example 1 were determined by standard methods by means of the dideoxy method (Sanger et al. (1977) Proc. Natl. Acad. Sci. USA, 74, 5463–5467). The nucleotide sequences (Seq. ID No. 1 to Sea. ID No. 3) are described above. The amino acid sequences derived therefrom are also given.

Example 3

Construct of the Plasmid p35s-anti-pot-SPS and Insertion of Gene 35s-anti-pot-SPS in the Genome of Potato Plants The gene 35s-anti-pot-SPS consists of the three fragments A, B and C (see FIG. 1).

The plasmid was prepared as follows:

From the pbluescript plasmid with the total insertion, an approximately 2 kb size fragment was prepared by EcoRV cleavage, and this was cloned in the SmaI cleavage site of the vector pBinAR (Höfgen & Willmitzer, 1990, Plant Sci., 66-221–230). The vector pBinAR is a derivative of the binary vector BIN 19 (Bevan, 1984, Nucl. Acids Res. 12: 8711–8721–8721) and was transferred using an *Agrobacterium tumefaciens* mediated transformation into potato. Intact, fertile plants were regenerated from the transformed cells.

As a result of the transformation, some transgenic potato plants were shown to have a reduced amount of RNA coding for the potato SPS (see FIG. 3). 50 µg total RNA in a Northern blot experiment was hybridised with the probe for SPS from potato.

Further the plants showed a reduction in SPS activity (see Table I).

Thus, by the transfer and expression of the gene 35s-anti-pot-SPS in potato plants, the amount of mRNA for the SPS protein which is formed, as well as the existing enzymatic activity can be significantly reduced.

Example 4

Figure 4:
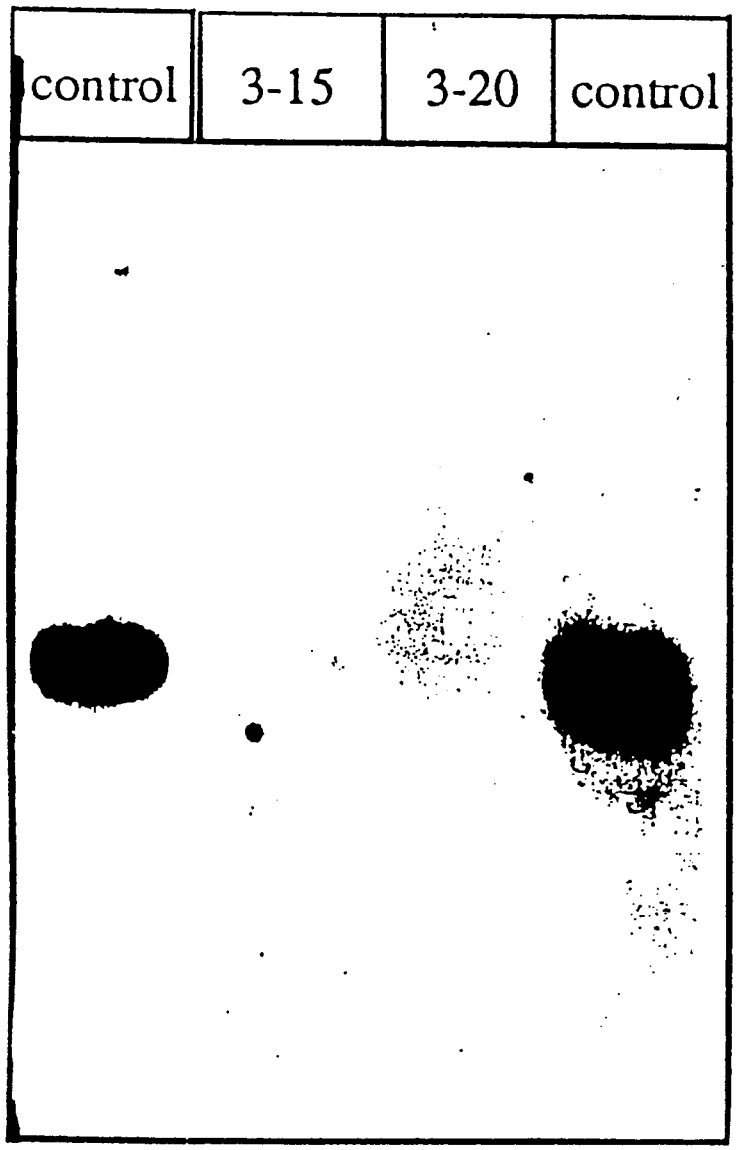
FIG. 4 is an analysis of plants transformed with a plasmid which included the B33-anti-pot-SPS gene.

Construct of Plasmid pB33-anti-pot-SpS and Insertion of Gene B33-anti-pot-SPS in the Genome of Potato Plants The gene B33-anti-pot-SPS consists of the three fragments A, B and C (see FIG. 4). The plasmid was prepared in an analogous method to that described in Example 3, except that a pBin 19 derivative was used as starting vector, which contains the B33 promoter of the patatin gene from *Solanum tuberosum* (Rocha-Sosa et al., 1989, EMBO J. 8: 23–29) in place of the 35S promoter of pBinAR.

The gene B33-anti-pot-SPS was transferred into potato plants using an *Agrobacterium tumefaciens* mediated transformation. Intact, fertile plants were regenerated from the transformed cells.

As a result of the transformation, some transgenic potato plants were shown with a reduced amount of RNA coding for the potato SPS (see FIG. 4). 50 µg total RNA in a Northern blot experiment was hybridised with the probe for SPS from potato.

Further the plants also showed a reduction of the SPS activity only in the tubers.

Thus, by the transfer and expression of the gene 35s-anti-pot-SPS in potato plants, the amount of mRNA for the SPS protein which is formed, as well as the existing enzymatic activity can be significantly reduced.

TABLE I

| Results of the transformation of potato plants | | | | |
|---|---|---|---|---|
| 1 | 2 | 3 | 4 | 5 |
| Control | 26.1 | 3.6 | 13.8 | 100 |
| 1-55 | 11.8 | 2.7 | 22.9 | 45 |
| 1-57 | 20.4 | 5.9 | 28.9 | 78 |
| 1-59 | 3.8 | 1.4 | 36.8 | 14.6 |
| 1-67 | 3.8 | 1.7 | 44.7 | 14.6 |
| 1-69 | 17.2 | 2.0 | 11.7 | 67 |
| 1-72 | 14.6 | 1.9 | 13.0 | 56 |
| 1-74 | 5.1 | 1.7 | 33.3 | 19.5 |

Column 1: Control = Wild type plants, numbers indicate individual transgenic plants
Column 2: Maximal speed of the enzyme reaction in the SPS activity test in nmol/min/mg.
Column 3: Speed in the SPS activity test in nmol/min/mg.
Column 4: Activity level of the SPS in %.
Column 5: Residual activity of the SPS in %.

What is claimed is:

1. A method for the preparation of a transgenic plant cell comprising the step of introducing a nucleic acid molecule comprising a DNA molecule from *Solanum tuberosum* encoding sucrose phosphate synthase into the genome of a plant cell.

2. A plant cell obtained by the method of claim 1.

3. A method for the preparation of a transgenic plant comprising the steps of introducing a nucleic acid molecule comprising a DNA molecule from *Solanum tuberosum* encoding sucrose phosphate synthase into the genome of a plant cell and regenerating a whole plant from the plant cell.

4. A plant obtained by the method of claim 3.

* * * * *

SEQUENCE LISTING

<160> NUMBER OF SEQ ID NOS: 6

<210> SEQ ID NO 1
<211> LENGTH: 3740
<212> TYPE: DNA

-continued

<213> ORGANISM: Solanum tuberosum
<220> FEATURE:
<221> NAME/KEY: CDS
<222> LOCATION: (957)..(3494)

<400> SEQUENCE: 1

```
ctattctctc ccctccttttt tctcctctct tcaaccccaa aacttccctt tcaaagcctt      60
tgctttccct ttctcactta cccagatcaa ctaagccaat ttgctgtagc ctcagaaaac     120
agcattccca gattgaaaaa gaatcttttt cagtacccaa aagttgggtt tctcatgtcc     180
agcaaggatt agctgctcta gctatttctt tagcccttaa ttttttgtcca gttgtgtctt    240 ctgattctgc attggcatct gaatttgatg tgttaaatga agggccacca aaggactcat    300
atgtagttga tgatgctggt gtgcttagca gggtgacaaa gtctgatttg aaggcattgt    360
tgtctgatgt ggagaagaga aaaggcttcc acattaattt catcactgtc cgcaagctca    420
ctagcaaagc tgatgctttt gagtatgctg accaagtttt ggagaagtgg tacctagtg    480 ttgaacaagg aaatgataag ggtatagttg tgcttgttac aagtcaaaag gaaggcgcaa    540
taaccggtgg ccctgatttt gtaaaggccg ttggagatac tgttcttgat gctaccgtct    600
cagagaacct tccagtgttg gctactgaag agaagtacaa tgaagcagtt ttcagcactg    660
ccacacgtct tgttgcagcc attgatggcc ttcctgatcc tggtggaccc caactcaagg    720
ataacaaaag agagtccaac ttcaaatcca gagaggaaac tgatgagaaa agaggacaat    780
tcacacttgt ggttggtggg ctgttagtga ttgcttttgt tgttcctatg gctcaatact    840
atgcatatgt ttcaaagaag tgaactgtct gattctggaa agttacattt tcgtgagatt    900
tgagtaagca tgtatattat cgtgtacaaa atggtccatt cggaaatgac tgattc atg    959
                                                                Met
                                                                 1 aga tat tta aaa agg ata aat atg aag att tgg acc tcc cct aac ata      1007
Arg Tyr Leu Lys Arg Ile Asn Met Lys Ile Trp Thr Ser Pro Asn Ile
        5                  10                  15 acg gat act gcc att tct ttt tca gag atg ctg acg cca ata agt aca      1055
Thr Asp Thr Ala Ile Ser Phe Ser Glu Met Leu Thr Pro Ile Ser Thr
    20                  25                  30 gac ggc ttg atg act gag atg ggg gag agt agt ggt gct tat att att      1103
Asp Gly Leu Met Thr Glu Met Gly Glu Ser Ser Gly Ala Tyr Ile Ile
 35                  40                  45 cgc att cct ttt gga cca aga gag aaa tat att cca aaa gaa cag cta      1151
Arg Ile Pro Phe Gly Pro Arg Glu Lys Tyr Ile Pro Lys Glu Gln Leu
50                  55                  60                  65 tgg ccc tat att ccc gaa ttt gtt gat ggt gca ctt aac cat att att      1199
Trp Pro Tyr Ile Pro Glu Phe Val Asp Gly Ala Leu Asn His Ile Ile
                70                  75                  80 caa atg tcc aaa gtt ctt ggg gag caa att ggt agt ggc tat cct gtg      1247
Gln Met Ser Lys Val Leu Gly Glu Gln Ile Gly Ser Gly Tyr Pro Val
            85                  90                  95 tgg cct gtt gcc ata cac gga cat tat gct gat gct ggc gac tca gct      1295
Trp Pro Val Ala Ile His Gly His Tyr Ala Asp Ala Gly Asp Ser Ala
        100                 105                 110 gct ctc ctg tca ggt gct tta aat gta cca atg ctt ttc act ggt cac      1343
Ala Leu Leu Ser Gly Ala Leu Asn Val Pro Met Leu Phe Thr Gly His
    115                 120                 125 tca ctt ggt aga gat aag ttg gag caa ctg ttg cga caa ggt cgt ttg      1391
Ser Leu Gly Arg Asp Lys Leu Glu Gln Leu Leu Arg Gln Gly Arg Leu
130                 135                 140                 145 tca aag gat gaa ata aac tca acc tac aag ata atg cgg aga ata gag      1439
Ser Lys Asp Glu Ile Asn Ser Thr Tyr Lys Ile Met Arg Arg Ile Glu
```

-continued

```
                     150                   155                   160
gct gaa gaa tta act ctt gat gct tcc gaa att gtc atc act agt aca    1487
Ala Glu Glu Leu Thr Leu Asp Ala Ser Glu Ile Val Ile Thr Ser Thr
            165                   170                   175 aga cag gag att gac gag caa tgg cgt ttg tat gat ggg ttt gat cca    1535
Arg Gln Glu Ile Asp Glu Gln Trp Arg Leu Tyr Asp Gly Phe Asp Pro
        180                   185                   190 ata tta gag cgt aag tta cgt gca agg atc aag cgc aat gtc agc tgt    1583
Ile Leu Glu Arg Lys Leu Arg Ala Arg Ile Lys Arg Asn Val Ser Cys
    195                   200                   205 tat ggc agg ttt atg cct cgt atg gct gta att cct cct ggg atg gag    1631
Tyr Gly Arg Phe Met Pro Arg Met Ala Val Ile Pro Pro Gly Met Glu
210                   215                   220                   225 ttc cac cat att gtg cca cat gaa ggt gac atg gat gga gaa aca gaa    1679
Phe His His Ile Val Pro His Glu Gly Asp Met Asp Gly Glu Thr Glu
                230                   235                   240 gga agt gaa gat ggg aag acc ccg gat cca cct att tgg gca gag att    1727
Gly Ser Glu Asp Gly Lys Thr Pro Asp Pro Pro Ile Trp Ala Glu Ile
            245                   250                   255 atg cgc ttc ttt tct aat cca agg aag cct atg ata ctc gca ctt gct    1775
Met Arg Phe Phe Ser Asn Pro Arg Lys Pro Met Ile Leu Ala Leu Ala
        260                   265                   270 agg cct gat ccc aag aag aac ctc act act tta gtg aaa gca ttt ggt    1823
Arg Pro Asp Pro Lys Lys Asn Leu Thr Thr Leu Val Lys Ala Phe Gly
    275                   280                   285 gaa tgt cgt cca ttg aga gag ctt gct aat ctt act ttg ata atg ggt    1871
Glu Cys Arg Pro Leu Arg Glu Leu Ala Asn Leu Thr Leu Ile Met Gly
290                   295                   300                   305 aat cga gat aat atc gac gaa atg tct agc acc aat tct gca ctt ctt    1919
Asn Arg Asp Asn Ile Asp Glu Met Ser Ser Thr Asn Ser Ala Leu Leu
                310                   315                   320 ctt tca atc ttg aaa atg ata gat aag tat gat ctt tat ggt caa gta    1967
Leu Ser Ile Leu Lys Met Ile Asp Lys Tyr Asp Leu Tyr Gly Gln Val
            325                   330                   335 gct tat cct aaa cac cac aag cag tca gat gtt cct gat atc tac cgt    2015
Ala Tyr Pro Lys His His Lys Gln Ser Asp Val Pro Asp Ile Tyr Arg
        340                   345                   350 ctt gct gca aag act aag ggt gtt ttt att aat cca gct ttt att gag    2063
Leu Ala Ala Lys Thr Lys Gly Val Phe Ile Asn Pro Ala Phe Ile Glu
    355                   360                   365 cct ttt gga ctg act ttg att gag gca gca gct tat ggt ctc cca atg    2111
Pro Phe Gly Leu Thr Leu Ile Glu Ala Ala Ala Tyr Gly Leu Pro Met
370                   375                   380                   385 gta gcc aca aaa aat gga gga cct gtt gat ata cat agg gtt ctt gac    2159
Val Ala Thr Lys Asn Gly Gly Pro Val Asp Ile His Arg Val Leu Asp
                390                   395                   400 aat ggt ctc tta gtg gat ccc cat gat cag cag gca att gct gat gct    2207
Asn Gly Leu Leu Val Asp Pro His Asp Gln Gln Ala Ile Ala Asp Ala
            405                   410                   415 ctt ttg aag ttg gtt gct gat aag caa ctg tgg gct aaa tgc agg gca    2255
Leu Leu Lys Leu Val Ala Asp Lys Gln Leu Trp Ala Lys Cys Arg Ala
        420                   425                   430 aat gga tta aaa aat atc cac ctt ttc tca tgg ccc gag cac tgt aaa    2303
Asn Gly Leu Lys Asn Ile His Leu Phe Ser Trp Pro Glu His Cys Lys
    435                   440                   445 act tat cta tcc cgg ata gct agc tgc aaa cca agg caa cca cgc tgg    2351
Thr Tyr Leu Ser Arg Ile Ala Ser Cys Lys Pro Arg Gln Pro Arg Trp
450                   455                   460                   465 ctg aga tcc att gat gat gat gat gaa aat tca gaa aca gat tca cct    2399
```

-continued

```
Leu Arg Ser Ile Asp Asp Asp Glu Asn Ser Glu Thr Asp Ser Pro
            470                 475                 480 agt gat tcc ttg aga gat att cat gat ata tct ctg aat ttg aga ttt    2447
Ser Asp Ser Leu Arg Asp Ile His Asp Ile Ser Leu Asn Leu Arg Phe
                485                 490                 495 tca tta gat ggg gaa aag aat gac aat aaa gaa aat gct gat aat aca    2495
Ser Leu Asp Gly Glu Lys Asn Asp Asn Lys Glu Asn Ala Asp Asn Thr
            500                 505                 510 tta gac ccc gaa gtt cga agg agc aag tta gag aat gct gtt ttg tcc    2543
Leu Asp Pro Glu Val Arg Arg Ser Lys Leu Glu Asn Ala Val Leu Ser
        515                 520                 525 tta tct aag ggt gca ctg aag agc aca tca aaa tct tgg tcg tca gac    2591
Leu Ser Lys Gly Ala Leu Lys Ser Thr Ser Lys Ser Trp Ser Ser Asp
530                 535                 540                 545 aag gca gac caa aac cct ggt gct ggt aaa ttc cca gcg att agg agg    2639
Lys Ala Asp Gln Asn Pro Gly Ala Gly Lys Phe Pro Ala Ile Arg Arg
                550                 555                 560 agg cga cat att ttt gtt att gca gtg gat tgt gat gct agc tca gga    2687
Arg Arg His Ile Phe Val Ile Ala Val Asp Cys Asp Ala Ser Ser Gly
                565                 570                 575 ctc tct gga agt gtg aaa aag ata ttt gag gct gta gag aag gaa agg    2735
Leu Ser Gly Ser Val Lys Lys Ile Phe Glu Ala Val Glu Lys Glu Arg
            580                 585                 590 gca gag ggt tcc att gga ttt atc ctg gct aca tct ttc aat ata tca    2783
Ala Glu Gly Ser Ile Gly Phe Ile Leu Ala Thr Ser Phe Asn Ile Ser
        595                 600                 605 gaa gta cag tct ttc ctg ctt tca gag ggc atg aat cct act gat ttt    2831
Glu Val Gln Ser Phe Leu Leu Ser Glu Gly Met Asn Pro Thr Asp Phe
610                 615                 620                 625 gat gct tac ata tgc aat agt ggt ggt gat ctt tat tat tcg tcc ttc    2879
Asp Ala Tyr Ile Cys Asn Ser Gly Gly Asp Leu Tyr Tyr Ser Ser Phe
                630                 635                 640 cat tct gag caa aat cct ttt gta gtt gac ttg tac tat cac tca cat    2927
His Ser Glu Gln Asn Pro Phe Val Val Asp Leu Tyr Tyr His Ser His
                645                 650                 655 att gag tat cgt tgg ggg ggc gaa gga ttg aga aag act ttg gtg cgt    2975
Ile Glu Tyr Arg Trp Gly Gly Glu Gly Leu Arg Lys Thr Leu Val Arg
            660                 665                 670 tgg gcc gcc tct atc att gat aag aat ggt gaa aat gga gat cac att    3023
Trp Ala Ala Ser Ile Ile Asp Lys Asn Gly Glu Asn Gly Asp His Ile
        675                 680                 685 gtt gtt gag gat gaa gac aat tca gct gac tac tgc tat act ttc aaa    3071
Val Val Glu Asp Glu Asp Asn Ser Ala Asp Tyr Cys Tyr Thr Phe Lys
690                 695                 700                 705 gtc tgc aag cct ggg acg gtt cct cca tct aaa gag ctt aga aaa gta    3119
Val Cys Lys Pro Gly Thr Val Pro Pro Ser Lys Glu Leu Arg Lys Val
                710                 715                 720 atg cga att cag gca ctt cgt tgt cac gct gtt tat tgt caa aat ggg    3167
Met Arg Ile Gln Ala Leu Arg Cys His Ala Val Tyr Cys Gln Asn Gly
                725                 730                 735 agt agg att aat gtg atc cct gta ctg gca tct cgg tcc caa gca ctc    3215
Ser Arg Ile Asn Val Ile Pro Val Leu Ala Ser Arg Ser Gln Ala Leu
            740                 745                 750 agg tac tta tat ctg cga tgg gga atg gac ttg tcg aag ttg gtg gtt    3263
Arg Tyr Leu Tyr Leu Arg Trp Gly Met Asp Leu Ser Lys Leu Val Val
        755                 760                 765 ttc gtc gga gaa agt ggt gat acc gat tat gaa gga tta atc ggt ggt    3311
Phe Val Gly Glu Ser Gly Asp Thr Asp Tyr Glu Gly Leu Ile Gly Gly
770                 775                 780                 785
```

```
                                                                            -continued cta cgc aag gct gtc ata atg aaa ggc ctc tgc act aat gca agc agc        3359
Leu Arg Lys Ala Val Ile Met Lys Gly Leu Cys Thr Asn Ala Ser Ser
            790                 795                 800 tta att cac ggt aat agg aat tac ccg cta tct gat gtt tta cca ttc        3407
Leu Ile His Gly Asn Arg Asn Tyr Pro Leu Ser Asp Val Leu Pro Phe
        805                 810                 815 gac agc cct aat gtc atc caa gcg gac gag gaa tgt agc agc acc gaa        3455
Asp Ser Pro Asn Val Ile Gln Ala Asp Glu Glu Cys Ser Ser Thr Glu
    820                 825                 830 atc cgt tgc tta ctg gtg aaa cta gcg gta ctc aaa gga taatacccctt        3504
Ile Arg Cys Leu Leu Val Lys Leu Ala Val Leu Lys Gly
835                 840                 845 ccccctttga ttgtcaaaaa cctatatgag ctataagact atgccatgaa aagaatggcc      3564
atccatttgg cttgtctttt gaagctgtta atacttttca acagactaca aaatgagatg      3624
agtcctttga tcctctttaa aggacataaa agctttatgc aagaaccagt gctgtaaagt      3684
tatagaattt cttttgctat atatgacatt cgacagaacc tgttccggtt catcga          3740

<210> SEQ ID NO 2
<211> LENGTH: 846
<212> TYPE: PRT
<213> ORGANISM: Solanum tuberosum

<400> SEQUENCE: 2

Met Arg Tyr Leu Lys Arg Ile Asn Met Lys Ile Trp Thr Ser Pro Asn
1               5                   10                  15

Ile Thr Asp Thr Ala Ile Ser Phe Ser Glu Met Leu Thr Pro Ile Ser
            20                  25                  30

Thr Asp Gly Leu Met Thr Glu Met Gly Glu Ser Ser Gly Ala Tyr Ile
        35                  40                  45

Ile Arg Ile Pro Phe Gly Pro Arg Glu Lys Tyr Ile Pro Lys Glu Gln
    50                  55                  60

Leu Trp Pro Tyr Ile Pro Glu Phe Val Asp Gly Ala Leu Asn His Ile
65                  70                  75                  80

Ile Gln Met Ser Lys Val Leu Gly Glu Gln Ile Gly Ser Gly Tyr Pro
                85                  90                  95

Val Trp Pro Val Ala Ile His Gly His Tyr Ala Asp Ala Gly Asp Ser
            100                 105                 110

Ala Ala Leu Leu Ser Gly Ala Leu Asn Val Pro Met Leu Phe Thr Gly
        115                 120                 125

His Ser Leu Gly Arg Asp Lys Leu Glu Gln Leu Leu Arg Gln Gly Arg
    130                 135                 140

Leu Ser Lys Asp Glu Ile Asn Ser Thr Tyr Lys Ile Met Arg Arg Ile
145                 150                 155                 160

Glu Ala Glu Glu Leu Thr Leu Asp Ala Ser Glu Ile Val Ile Thr Ser
                165                 170                 175

Thr Arg Gln Glu Ile Asp Glu Gln Trp Arg Leu Tyr Asp Gly Phe Asp
            180                 185                 190

Pro Ile Leu Glu Arg Lys Leu Arg Ala Arg Ile Lys Arg Asn Val Ser
        195                 200                 205

Cys Tyr Gly Arg Phe Met Pro Arg Met Ala Val Ile Pro Pro Gly Met
    210                 215                 220

Glu Phe His His Ile Val Pro His Gly Asp Met Asp Gly Glu Thr
225                 230                 235                 240

Glu Gly Ser Glu Asp Gly Lys Thr Pro Asp Pro Ile Trp Ala Glu
                245                 250                 255
```

-continued

```
Ile Met Arg Phe Phe Ser Asn Pro Arg Lys Pro Met Ile Leu Ala Leu
        260                 265                 270

Ala Arg Pro Asp Pro Lys Lys Asn Leu Thr Thr Leu Val Lys Ala Phe
        275                 280                 285

Gly Glu Cys Arg Pro Leu Arg Glu Leu Ala Asn Leu Thr Leu Ile Met
        290                 295                 300

Gly Asn Arg Asp Asn Ile Asp Glu Met Ser Ser Thr Asn Ser Ala Leu
305                 310                 315                 320

Leu Leu Ser Ile Leu Lys Met Ile Asp Lys Tyr Asp Leu Tyr Gly Gln
                325                 330                 335

Val Ala Tyr Pro Lys His His Lys Gln Ser Asp Val Pro Asp Ile Tyr
        340                 345                 350

Arg Leu Ala Ala Lys Thr Lys Gly Val Phe Ile Asn Pro Ala Phe Ile
        355                 360                 365

Glu Pro Phe Gly Leu Thr Leu Ile Glu Ala Ala Tyr Gly Leu Pro
        370                 375                 380

Met Val Ala Thr Lys Asn Gly Gly Pro Val Asp Ile His Arg Val Leu
385                 390                 395                 400

Asp Asn Gly Leu Leu Val Asp Pro His Asp Gln Gln Ala Ile Ala Asp
                405                 410                 415

Ala Leu Leu Lys Leu Val Ala Asp Lys Gln Leu Trp Ala Lys Cys Arg
                420                 425                 430

Ala Asn Gly Leu Lys Asn Ile His Leu Phe Ser Trp Pro Glu His Cys
                435                 440                 445

Lys Thr Tyr Leu Ser Arg Ile Ala Ser Cys Lys Pro Arg Gln Pro Arg
        450                 455                 460

Trp Leu Arg Ser Ile Asp Asp Asp Glu Asn Ser Glu Thr Asp Ser
465                 470                 475                 480

Pro Ser Asp Ser Leu Arg Asp Ile His Asp Ile Ser Leu Asn Leu Arg
                485                 490                 495

Phe Ser Leu Asp Gly Glu Lys Asn Asp Asn Lys Glu Asn Ala Asp Asn
        500                 505                 510

Thr Leu Asp Pro Glu Val Arg Arg Ser Lys Leu Glu Asn Ala Val Leu
        515                 520                 525

Ser Leu Ser Lys Gly Ala Leu Lys Ser Thr Ser Lys Ser Trp Ser Ser
        530                 535                 540

Asp Lys Ala Asp Gln Asn Pro Gly Ala Gly Lys Phe Pro Ala Ile Arg
545                 550                 555                 560

Arg Arg Arg His Ile Phe Val Ile Ala Val Asp Cys Asp Ala Ser Ser
                565                 570                 575

Gly Leu Ser Gly Ser Val Lys Lys Ile Phe Glu Ala Val Glu Lys Glu
                580                 585                 590

Arg Ala Glu Gly Ser Ile Gly Phe Ile Leu Ala Thr Ser Phe Asn Ile
        595                 600                 605

Ser Glu Val Gln Ser Phe Leu Leu Ser Glu Gly Met Asn Pro Thr Asp
        610                 615                 620

Phe Asp Ala Tyr Ile Cys Asn Ser Gly Gly Asp Leu Tyr Tyr Ser Ser
625                 630                 635                 640

Phe His Ser Glu Gln Asn Pro Phe Val Val Asp Leu Tyr Tyr His Ser
                645                 650                 655

His Ile Glu Tyr Arg Trp Gly Gly Glu Gly Leu Arg Lys Thr Leu Val
                660                 665                 670
```

```
Arg Trp Ala Ala Ser Ile Ile Asp Lys Asn Gly Glu Asn Gly Asp His
            675                 680                 685

Ile Val Val Glu Asp Glu Asp Asn Ser Ala Asp Tyr Cys Tyr Thr Phe
        690                 695                 700

Lys Val Cys Lys Pro Gly Thr Val Pro Pro Ser Lys Glu Leu Arg Lys
705                 710                 715                 720

Val Met Arg Ile Gln Ala Leu Arg Cys His Ala Val Tyr Cys Gln Asn
                725                 730                 735

Gly Ser Arg Ile Asn Val Ile Pro Val Leu Ala Ser Arg Ser Gln Ala
            740                 745                 750

Leu Arg Tyr Leu Tyr Leu Arg Trp Gly Met Asp Leu Ser Lys Leu Val
        755                 760                 765

Val Phe Val Gly Glu Ser Gly Asp Thr Asp Tyr Glu Gly Leu Ile Gly
    770                 775                 780

Gly Leu Arg Lys Ala Val Ile Met Lys Gly Leu Cys Thr Asn Ala Ser
785                 790                 795                 800

Ser Leu Ile His Gly Asn Arg Asn Tyr Pro Leu Ser Asp Val Leu Pro
                805                 810                 815

Phe Asp Ser Pro Asn Val Ile Gln Ala Asp Glu Glu Cys Ser Ser Thr
            820                 825                 830

Glu Ile Arg Cys Leu Leu Val Lys Leu Ala Val Leu Lys Gly
        835                 840                 845

<210> SEQ ID NO 3
<211> LENGTH: 3625
<212> TYPE: DNA
<213> ORGANISM: Solanum tuberosum
<220> FEATURE:
<221> NAME/KEY: CDS
<222> LOCATION: (121)..(3282)

<400> SEQUENCE: 3
atttttttct ctaagttctc tctcgctgtc cttatcattt caccacctcc ataaatctag      60
aaacatcttt tctactccgt taatctctct agcacacggc ggaggagtgc ggcggaggag     120 atg gcg gga aac gat tgg att aac agt tac tta gag gcg ata ctg gat      168
Met Ala Gly Asn Asp Trp Ile Asn Ser Tyr Leu Glu Ala Ile Leu Asp
1               5                   10                  15 gtt gga cca ggg cta gat gat aag aag tca tcg ttg ttg ttg aga gaa      216
Val Gly Pro Gly Leu Asp Asp Lys Lys Ser Ser Leu Leu Leu Arg Glu
                20                  25                  30 aga ggg agg ttt agt ccg acg agg tac ttt gtt gag gaa gtt att act      264
Arg Gly Arg Phe Ser Pro Thr Arg Tyr Phe Val Glu Glu Val Ile Thr
            35                  40                  45 gga ttc gat gag act gat ttg cat cgt tcg tgg atc cga gca caa gct      312
Gly Phe Asp Glu Thr Asp Leu His Arg Ser Trp Ile Arg Ala Gln Ala
        50                  55                  60 act cgg agt ccg cag aga agg aat act agg ctc gag aat atg tgc tgg      360
Thr Arg Ser Pro Gln Arg Arg Asn Thr Arg Leu Glu Asn Met Cys Trp
65                  70                  75                  80 agg att tgg aat ttg gct cgc cag aaa aag cag ctt gag gga gag caa      408
Arg Ile Trp Asn Leu Ala Arg Gln Lys Lys Gln Leu Glu Gly Glu Gln
                85                  90                  95 gct cag tgg atg gca aaa cgc cgt caa gaa cgt gaa aga ggt cgc aga      456
Ala Gln Trp Met Ala Lys Arg Arg Gln Glu Arg Glu Arg Gly Arg Arg
                100                 105                 110 gaa gca gtt gct gat atg tca gag gat cta tct gag gga gag aaa gga      504
Glu Ala Val Ala Asp Met Ser Glu Asp Leu Ser Glu Gly Glu Lys Gly
```

-continued

```
            115                 120                 125
gat ata gtc gct gac atg tca tct cat ggt gaa agt acc aga ggc cga    552
Asp Ile Val Ala Asp Met Ser Ser His Gly Glu Ser Thr Arg Gly Arg
        130                 135                 140 ttg cct aga atc agt tct gtt gag aca atg gaa gca tgg gtc agt cag    600
Leu Pro Arg Ile Ser Ser Val Glu Thr Met Glu Ala Trp Val Ser Gln
145                 150                 155                 160 cag aga gga aag aag ctt tat atc gtg ctt ata agt tta cat ggt tta    648
Gln Arg Gly Lys Lys Leu Tyr Ile Val Leu Ile Ser Leu His Gly Leu
                165                 170                 175 att cgg ggt gag aat atg gag ctt gga cgg gat tct gat act ggt ggt    696
Ile Arg Gly Glu Asn Met Glu Leu Gly Arg Asp Ser Asp Thr Gly Gly
            180                 185                 190 cag gtg aag tat gtt gtt gaa ctt gcg agg gcc tta ggg tcg atg cca    744
Gln Val Lys Tyr Val Val Glu Leu Ala Arg Ala Leu Gly Ser Met Pro
        195                 200                 205 ggt gta tat cgg gtt gac ttg ctt act aga caa gta tct tca cca gaa    792
Gly Val Tyr Arg Val Asp Leu Leu Thr Arg Gln Val Ser Ser Pro Glu
    210                 215                 220 gta gat tgg agc tat ggt gag ccg aca gag atg ctg acg cca ata agt    840
Val Asp Trp Ser Tyr Gly Glu Pro Thr Glu Met Leu Thr Pro Ile Ser
225                 230                 235                 240 aca gac ggc ttg atg act gag atg ggg gag agt agt ggt gct tat att    888
Thr Asp Gly Leu Met Thr Glu Met Gly Glu Ser Ser Gly Ala Tyr Ile
                245                 250                 255 att cgc att cct ttt gga cca aga gag aaa tat att cca aaa gaa cag    936
Ile Arg Ile Pro Phe Gly Pro Arg Glu Lys Tyr Ile Pro Lys Glu Gln
            260                 265                 270 cta tgg ccc tat att ccc gaa ttt gtt gat ggt gca ctt aac cat att    984
Leu Trp Pro Tyr Ile Pro Glu Phe Val Asp Gly Ala Leu Asn His Ile
        275                 280                 285 att caa atg tcc aaa gtt ctt ggg gag caa att ggt agt ggc tat cct   1032
Ile Gln Met Ser Lys Val Leu Gly Glu Gln Ile Gly Ser Gly Tyr Pro
    290                 295                 300 gtg tgg cct gtt gcc ata cac gga cat tat gct gat gct ggc gac tca   1080
Val Trp Pro Val Ala Ile His Gly His Tyr Ala Asp Ala Gly Asp Ser
305                 310                 315                 320 gct gct ctc ctg tca ggt gct tta aat gta cca atg ctt ttc act ggt   1128
Ala Ala Leu Leu Ser Gly Ala Leu Asn Val Pro Met Leu Phe Thr Gly
                325                 330                 335 cac tca ctt ggt aga gat aag ttg gag caa ctg ttg gca caa ggt cga   1176
His Ser Leu Gly Arg Asp Lys Leu Glu Gln Leu Leu Ala Gln Gly Arg
            340                 345                 350 aag tca aag gat gaa ata aac tca acc tac aag ata atg cgg aga ata   1224
Lys Ser Lys Asp Glu Ile Asn Ser Thr Tyr Lys Ile Met Arg Arg Ile
        355                 360                 365 gag gct gaa gaa tta act ctt gat gct tcc gaa att gtc atc act agt   1272
Glu Ala Glu Glu Leu Thr Leu Asp Ala Ser Glu Ile Val Ile Thr Ser
    370                 375                 380 aca aga cag gag att gac gag caa tgg cgt ttg tat gat ggg ttt gat   1320
Thr Arg Gln Glu Ile Asp Glu Gln Trp Arg Leu Tyr Asp Gly Phe Asp
385                 390                 395                 400 cca ata tta gag cgt aag tta cgt gca agg atc aag cgc aat gtc agc   1368
Pro Ile Leu Glu Arg Lys Leu Arg Ala Arg Ile Lys Arg Asn Val Ser
                405                 410                 415 tgt tat ggc agg ttt atg cct cgt atg gct gta att cct cct ggg atg   1416
Cys Tyr Gly Arg Phe Met Pro Arg Met Ala Val Ile Pro Pro Gly Met
            420                 425                 430 gag ttc cac cat att gtg cca cat gaa ggt gac atg gat ggt gaa aca   1464
```

-continued

| | | |
|---|---|---|
| Glu Phe His His Ile Val Pro His Glu Gly Asp Met Asp Gly Glu Thr<br>                          435                       440                       445 | | |
| gaa gga agt gaa gat ggg aag acc ccg gat cca cct att tgg gca gag<br>Glu Gly Ser Glu Asp Gly Lys Thr Pro Asp Pro Pro Ile Trp Ala Glu<br>450                           455                       460 | 1512 | |
| att atg cgc ttc ttt tct aat cca agg aag cct atg ata ctc gca ctt<br>Ile Met Arg Phe Phe Ser Asn Pro Arg Lys Pro Met Ile Leu Ala Leu<br>465                        470                       475                  480 | 1560 | |
| gct agg cct gat ccc aag aag aac ctc act act tta gtg aaa gca ttt<br>Ala Arg Pro Asp Pro Lys Lys Asn Leu Thr Thr Leu Val Lys Ala Phe<br>                       485                       490                       495 | 1608 | |
| ggt gaa tgt cgt cca ttg aga gag ctt gct aat ctt act ttg ata atg<br>Gly Glu Cys Arg Pro Leu Arg Glu Leu Ala Asn Leu Thr Leu Ile Met<br>         500                       505                       510 | 1656 | |
| ggt aat cga gat aat atc gac gaa atg tct agc acc aat tct gca ctt<br>Gly Asn Arg Asp Asn Ile Asp Glu Met Ser Ser Thr Asn Ser Ala Leu<br>         515                       520                       525 | 1704 | |
| ctt ctt tca atc ttg aaa atg ata gat aag tat gat ctt tat ggt caa<br>Leu Leu Ser Ile Leu Lys Met Ile Asp Lys Tyr Asp Leu Tyr Gly Gln<br>               530                       535                       540 | 1752 | |
| gta gct tat cct aaa cac cac aag cag tca gat gtt cct gat atc tac<br>Val Ala Tyr Pro Lys His His Lys Gln Ser Asp Val Pro Asp Ile Tyr<br>545                        550                       555                  560 | 1800 | |
| cgt ctt gct gca aag act aag ggt gtt ttt att aat cca gct ttt att<br>Arg Leu Ala Ala Lys Thr Lys Gly Val Phe Ile Asn Pro Ala Phe Ile<br>                       565                       570                       575 | 1848 | |
| gag cct ttt gga ctg act ttg att gag gca gca gct tat ggt ctc cca<br>Glu Pro Phe Gly Leu Thr Leu Ile Glu Ala Ala Ala Tyr Gly Leu Pro<br>               580                       585                       590 | 1896 | |
| atg gta gcc aca aaa aat gga gga cct gtt gat ata cat agg gtt ctt<br>Met Val Ala Thr Lys Asn Gly Gly Pro Val Asp Ile His Arg Val Leu<br>         595                       600                       605 | 1944 | |
| gac aat ggt ctc tta gtg gat ccc cat gat cag cag gca att gct gat<br>Asp Asn Gly Leu Leu Val Asp Pro His Asp Gln Gln Ala Ile Ala Asp<br>         610                       615                       620 | 1992 | |
| gct ctt ttg aag ttg gtt gct gat aag caa ctg tgg gct aaa tgc agg<br>Ala Leu Leu Lys Leu Val Ala Asp Lys Gln Leu Trp Ala Lys Cys Arg<br>625                        630                       635                  640 | 2040 | |
| gca aat gga tta aaa aat atc cac ctt ttc tca tgg ccc gag cac tgt<br>Ala Asn Gly Leu Lys Asn Ile His Leu Phe Ser Trp Pro Glu His Cys<br>                       645                       650                       655 | 2088 | |
| aaa act tat cta tcc cgg ata gct agc tgc aaa cca agg caa cca cgc<br>Lys Thr Tyr Leu Ser Arg Ile Ala Ser Cys Lys Pro Arg Gln Pro Arg<br>               660                       665                       670 | 2136 | |
| tgg ctg aga tcc att gat gat gat gat gaa aat tca gaa aca gat tca<br>Trp Leu Arg Ser Ile Asp Asp Asp Asp Glu Asn Ser Glu Thr Asp Ser<br>               675                       680                       685 | 2184 | |
| cct agt gat tcc ttg aga gat att cat gat ata tct ctg aat ttg aga<br>Pro Ser Asp Ser Leu Arg Asp Ile His Asp Ile Ser Leu Asn Leu Arg<br>690                        695                       700 | 2232 | |
| ttt tca tta gat ggg gaa aag aat gac aat aaa gaa aat gct gat aat<br>Phe Ser Leu Asp Gly Glu Lys Asn Asp Asn Lys Glu Asn Ala Asp Asn<br>705                        710                       715                  720 | 2280 | |
| aca tta gac ccc gaa gtt cga agg agc aag tta gag aat gct gtt ttg<br>Thr Leu Asp Pro Glu Val Arg Arg Ser Lys Leu Glu Asn Ala Val Leu<br>                       725                       730                       735 | 2328 | |
| tcc tta tct aag ggt gca ctg aag agc aca tca aaa tct tgg tcg tca<br>Ser Leu Ser Lys Gly Ala Leu Lys Ser Thr Ser Lys Ser Trp Ser Ser<br>         740                       745                       750 | 2376 | |

-continued

| | |
|---|---|
| gac aag gca gac caa aac cct ggt gct ggt aaa ttc cca gcg att agg<br>Asp Lys Ala Asp Gln Asn Pro Gly Ala Gly Lys Phe Pro Ala Ile Arg<br>755                    760                      765 | 2424 |
| agg agg cga cat att ttt gtt att gca gtg gat tgt gat gct agc tca<br>Arg Arg Arg His Ile Phe Val Ile Ala Val Asp Cys Asp Ala Ser Ser<br>770                    775                    780 | 2472 |
| gga ctc tct gga agt gtg aaa aag ata ttt gag gct gta gag aag gaa<br>Gly Leu Ser Gly Ser Val Lys Lys Ile Phe Glu Ala Val Glu Lys Glu<br>785                    790                    795                    800 | 2520 |
| agg gca gag ggt tcc att gga ttt atc ctg gct aca tct ttc aat ata<br>Arg Ala Glu Gly Ser Ile Gly Phe Ile Leu Ala Thr Ser Phe Asn Ile<br>                  805                    810                    815 | 2568 |
| tca gaa gta cag tct ttc ctg ctt tca gag ggc atg aat cct act gat<br>Ser Glu Val Gln Ser Phe Leu Leu Ser Glu Gly Met Asn Pro Thr Asp<br>820                    825                    830 | 2616 |
| ttt gat gct tac ata tgc aat agt ggt ggt gat ctt tat tat tcg tcc<br>Phe Asp Ala Tyr Ile Cys Asn Ser Gly Gly Asp Leu Tyr Tyr Ser Ser<br>835                    840                    845 | 2664 |
| ttc cat tct gag caa aat cct ttt gta gtt gac ttg tac tat cac tca<br>Phe His Ser Glu Gln Asn Pro Phe Val Val Asp Leu Tyr Tyr His Ser<br>850                    855                    860 | 2712 |
| cat att gag tat cgt tgg ggg ggc gaa gga ttg aga aag act ttg gtg<br>His Ile Glu Tyr Arg Trp Gly Gly Glu Gly Leu Arg Lys Thr Leu Val<br>865                    870                    875                    880 | 2760 |
| cgt tgg gcc gcc tct atc att gat aag aat ggt gaa aat gga gat cac<br>Arg Trp Ala Ala Ser Ile Ile Asp Lys Asn Gly Glu Asn Gly Asp His<br>                  885                    890                    895 | 2808 |
| att gtt gtt gag gat gaa gac aat tca gct gac tac tgc tat act ttc<br>Ile Val Val Glu Asp Glu Asp Asn Ser Ala Asp Tyr Cys Tyr Thr Phe<br>                  900                    905                    910 | 2856 |
| aaa gtc tgc aag cct ggg acg gtt cct cca tct aaa gag ctt aga aaa<br>Lys Val Cys Lys Pro Gly Thr Val Pro Pro Ser Lys Glu Leu Arg Lys<br>                  915                    920                    925 | 2904 |
| gta atg cga att cag gca ctt cgt tgt cac gct gtt tat tgt caa aat<br>Val Met Arg Ile Gln Ala Leu Arg Cys His Ala Val Tyr Cys Gln Asn<br>930                    935                    940 | 2952 |
| ggg agt agg att aat gtg atc cct gta ctg gca tct cgg tcc caa gca<br>Gly Ser Arg Ile Asn Val Ile Pro Val Leu Ala Ser Arg Ser Gln Ala<br>945                    950                    955                    960 | 3000 |
| ctc agg tac tta tat ctg cga tgg gga atg gac ttg tcg aag ttg gtg<br>Leu Arg Tyr Leu Tyr Leu Arg Trp Gly Met Asp Leu Ser Lys Leu Val<br>                  965                    970                    975 | 3048 |
| gtt ttc gtc gga gaa agt ggt gat acc gat tat gaa gga tta atc ggt<br>Val Phe Val Gly Glu Ser Gly Asp Thr Asp Tyr Glu Gly Leu Ile Gly<br>980                    985                    990 | 3096 |
| ggt cta cgc aag gct gtc ata atg aaa ggc ctc tgc act aat gca agc<br>Gly Leu Arg Lys Ala Val Ile Met Lys Gly Leu Cys Thr Asn Ala Ser<br>995                    1000                    1005 | 3144 |
| agc tta att cac ggt aat agg aat tac ccg cta tct gat gtt tta cca<br>Ser Leu Ile His Gly Asn Arg Asn Tyr Pro Leu Ser Asp Val Leu Pro<br>1010                   1015                 1020 | 3192 |
| ttc gac agc cct aat gtc atc caa gcg gac gag gaa tgt agc agc acc<br>Phe Asp Ser Pro Asn Val Ile Gln Ala Asp Glu Glu Cys Ser Ser Thr<br>1025                 1030                 1035                 1040 | 3240 |
| gaa atc cgt tgc tta ctg gag aaa cta gcg gta ctc aaa gga<br>Glu Ile Arg Cys Leu Leu Glu Lys Leu Ala Val Leu Lys Gly<br>1045                 1050 | 3282 |
| taatacccctt ccccctttga ttgtcaaaaa cctatatgag ctataagact atgccatgaa | 3342 |
| aagaatggcc atccatttgg cttgtctttt gaagctgtta atactttca acagactaca | 3402 |

-continued

```
aaatgagatg agtcctttga tcctctttaa aggacataaa agctttatgc aagaaccagt    3462
gctgtaaagt tatagaattt cttttgctat atatgacatt cgacagaacc agttccggtt    3522
catcgagaaa aagaaataaa tttcaactta taaacatgcc tgatcatgta aattatcata    3582
tacatccatc ggaaggcatt atcgatgggt tatcagattt ttt                      3625
```

<210> SEQ ID NO 4
<211> LENGTH: 1054
<212> TYPE: PRT
<213> ORGANISM: Solanum tuberosum

<400> SEQUENCE: 4

```
Met Ala Gly Asn Asp Trp Ile Asn Ser Tyr Leu Glu Ala Ile Leu Asp
  1               5                  10                  15

Val Gly Pro Gly Leu Asp Asp Lys Lys Ser Leu Leu Leu Arg Glu
             20                  25                  30

Arg Gly Arg Phe Ser Pro Thr Arg Tyr Phe Val Glu Glu Val Ile Thr
         35                  40                  45

Gly Phe Asp Glu Thr Asp Leu His Arg Ser Trp Ile Arg Ala Gln Ala
     50                  55                  60

Thr Arg Ser Pro Gln Arg Arg Asn Thr Arg Leu Glu Asn Met Cys Trp
 65                  70                  75                  80

Arg Ile Trp Asn Leu Ala Arg Gln Lys Lys Gln Leu Glu Gly Glu Gln
                 85                  90                  95

Ala Gln Trp Met Ala Lys Arg Arg Gln Glu Arg Glu Arg Gly Arg Arg
            100                 105                 110

Glu Ala Val Ala Asp Met Ser Glu Asp Leu Ser Glu Gly Glu Lys Gly
        115                 120                 125

Asp Ile Val Ala Asp Met Ser Ser His Gly Glu Ser Thr Arg Gly Arg
    130                 135                 140

Leu Pro Arg Ile Ser Ser Val Glu Thr Met Glu Ala Trp Val Ser Gln
145                 150                 155                 160

Gln Arg Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Glu Leu Ala Arg Ala Leu Gly Ser Met Pro
        195                 200                 205

Gly Val Tyr Arg Val Asp Leu Leu Thr Arg Gln Val Ser Ser Pro Glu
    210                 215                 220

Val Asp Trp Ser Tyr Gly Glu Pro Thr Glu Met Leu Thr Pro Ile Ser
225                 230                 235                 240

Thr Asp Gly Leu Met Thr Glu Met Gly Glu Ser Ser Gly Ala Tyr Ile
                245                 250                 255

Ile Arg Ile Pro Phe Gly Pro Arg Glu Lys Tyr Ile Pro Lys Glu Gln
            260                 265                 270

Leu Trp Pro Tyr Ile Pro Glu Phe Val Asp Gly Ala Leu Asn His Ile
        275                 280                 285

Ile Gln Met Ser Lys Val Leu Gly Glu Gln Ile Gly Ser Gly Tyr Pro
    290                 295                 300

Val Trp Pro Val Ala Ile His Gly His Tyr Ala Asp Ala Gly Asp Ser
305                 310                 315                 320

Ala Ala Leu Leu Ser Gly Ala Leu Asn Val Pro Met Leu Phe Thr Gly
                325                 330                 335
```

-continued

```
His Ser Leu Gly Arg Asp Lys Leu Glu Gln Leu Leu Ala Gln Gly Arg
            340                 345                 350
Lys Ser Lys Asp Glu Ile Asn Ser Thr Tyr Lys Ile Met Arg Arg Ile
        355                 360                 365
Glu Ala Glu Glu Leu Thr Leu Asp Ala Ser Glu Ile Val Ile Thr Ser
    370                 375                 380
Thr Arg Gln Glu Ile Asp Glu Gln Trp Arg Leu Tyr Asp Gly Phe Asp
385                 390                 395                 400
Pro Ile Leu Glu Arg Lys Leu Arg Ala Arg Ile Lys Arg Asn Val Ser
                405                 410                 415
Cys Tyr Gly Arg Phe Met Pro Arg Met Ala Val Ile Pro Pro Gly Met
            420                 425                 430
Glu Phe His His Ile Val Pro His Glu Gly Asp Met Asp Gly Glu Thr
        435                 440                 445
Glu Gly Ser Glu Asp Gly Lys Thr Pro Asp Pro Ile Trp Ala Glu
    450                 455                 460
Ile Met Arg Phe Phe Ser Asn Pro Arg Lys Pro Met Ile Leu Ala Leu
465                 470                 475                 480
Ala Arg Pro Asp Pro Lys Lys Asn Leu Thr Thr Leu Val Lys Ala Phe
                485                 490                 495
Gly Glu Cys Arg Pro Leu Arg Glu Leu Ala Asn Leu Thr Leu Ile Met
            500                 505                 510
Gly Asn Arg Asp Asn Ile Asp Glu Met Ser Ser Thr Asn Ser Ala Leu
        515                 520                 525
Leu Leu Ser Ile Leu Lys Met Ile Asp Lys Tyr Asp Leu Tyr Gly Gln
    530                 535                 540
Val Ala Tyr Pro Lys His His Lys Gln Ser Asp Val Pro Asp Ile Tyr
545                 550                 555                 560
Arg Leu Ala Ala Lys Thr Lys Gly Val Phe Ile Asn Pro Ala Phe Ile
                565                 570                 575
Glu Pro Phe Gly Leu Thr Leu Ile Glu Ala Ala Ala Tyr Gly Leu Pro
            580                 585                 590
Met Val Ala Thr Lys Asn Gly Gly Pro Val Asp Ile His Arg Val Leu
        595                 600                 605
Asp Asn Gly Leu Leu Val Asp Pro His Asp Gln Gln Ala Ile Ala Asp
    610                 615                 620
Ala Leu Leu Lys Leu Val Ala Asp Lys Gln Leu Trp Ala Lys Cys Arg
625                 630                 635                 640
Ala Asn Gly Leu Lys Asn Ile His Leu Phe Ser Trp Pro Glu His Cys
                645                 650                 655
Lys Thr Tyr Leu Ser Arg Ile Ala Ser Cys Lys Pro Arg Gln Pro Arg
            660                 665                 670
Trp Leu Arg Ser Ile Asp Asp Asp Glu Asn Ser Glu Thr Asp Ser
        675                 680                 685
Pro Ser Asp Ser Leu Arg Asp Ile His Asp Ile Ser Leu Asn Leu Arg
    690                 695                 700
Phe Ser Leu Asp Gly Glu Lys Asn Asp Asn Lys Glu Asn Ala Asp Asn
705                 710                 715                 720
Thr Leu Asp Pro Glu Val Arg Arg Ser Lys Leu Glu Asn Ala Val Leu
                725                 730                 735
Ser Leu Ser Lys Gly Ala Leu Lys Ser Thr Ser Lys Ser Trp Ser Ser
            740                 745                 750
```

-continued

```
Asp Lys Ala Asp Gln Asn Pro Gly Ala Gly Lys Phe Pro Ala Ile Arg
        755                 760                 765

Arg Arg Arg His Ile Phe Val Ile Ala Val Asp Cys Asp Ala Ser Ser
    770                 775                 780

Gly Leu Ser Gly Ser Val Lys Lys Ile Phe Glu Ala Val Glu Lys Glu
785                 790                 795                 800

Arg Ala Glu Gly Ser Ile Gly Phe Ile Leu Ala Thr Ser Phe Asn Ile
                805                 810                 815

Ser Glu Val Gln Ser Phe Leu Leu Ser Glu Gly Met Asn Pro Thr Asp
                    820                 825                 830

Phe Asp Ala Tyr Ile Cys Asn Ser Gly Gly Asp Leu Tyr Tyr Ser Ser
            835                 840                 845

Phe His Ser Glu Gln Asn Pro Phe Val Val Asp Leu Tyr Tyr His Ser
    850                 855                 860

His Ile Glu Tyr Arg Trp Gly Gly Glu Gly Leu Arg Lys Thr Leu Val
865                 870                 875                 880

Arg Trp Ala Ala Ser Ile Ile Asp Lys Asn Gly Glu Asn Gly Asp His
                885                 890                 895

Ile Val Val Glu Asp Glu Asp Asn Ser Ala Asp Tyr Cys Tyr Thr Phe
                900                 905                 910

Lys Val Cys Lys Pro Gly Thr Val Pro Pro Ser Lys Glu Leu Arg Lys
            915                 920                 925

Val Met Arg Ile Gln Ala Leu Arg Cys His Ala Val Tyr Cys Gln Asn
930                 935                 940

Gly Ser Arg Ile Asn Val Ile Pro Val Leu Ala Ser Arg Ser Gln Ala
945                 950                 955                 960

Leu Arg Tyr Leu Tyr Leu Arg Trp Gly Met Asp Leu Ser Lys Leu Val
                965                 970                 975

Val Phe Val Gly Glu Ser Gly Asp Thr Asp Tyr Glu Gly Leu Ile Gly
            980                 985                 990

Gly Leu Arg Lys Ala Val Ile Met Lys Gly Leu Cys Thr Asn Ala Ser
        995                 1000                1005

Ser Leu Ile His Gly Asn Arg Asn Tyr Pro Leu Ser Asp Val Leu Pro
    1010                1015                1020

Phe Asp Ser Pro Asn Val Ile Gln Ala Asp Glu Glu Cys Ser Ser Thr
1025                1030                1035                1040

Glu Ile Arg Cys Leu Leu Glu Lys Leu Ala Val Leu Lys Gly
                1045                1050

<210> SEQ ID NO 5
<211> LENGTH: 2930
<212> TYPE: DNA
<213> ORGANISM: Solanum tuberosum
<220> FEATURE:
<221> NAME/KEY: CDS
<222> LOCATION: (118)..(2841)

<400> SEQUENCE: 5 attttttttct ctaaattctc tctcactgtc cttatcattt caccacctcc ataaatctag      60
aaacatcttt tctattccgt taatctctct agcacacggc ggagtgcggc ggaggag         117 atg gcg gga aac gac tgg att aac agt tac tta gag gcg ata ctg gat      165
Met Ala Gly Asn Asp Trp Ile Asn Ser Tyr Leu Glu Ala Ile Leu Asp
 1               5                  10                  15 gta gga cca ggg cta gat gat aag aaa tca tcg ttg ttg ttg aga gaa      213
Val Gly Pro Gly Leu Asp Asp Lys Lys Ser Ser Leu Leu Leu Arg Glu
```

```
                   20                  25                  30
aga ggg agg ttt agt ccg acg agg tac ttt gtt gag gaa gtt att act        261
Arg Gly Arg Phe Ser Pro Thr Arg Tyr Phe Val Glu Glu Val Ile Thr
         35                  40                  45 gga ttc gat gag act gat ttg cat cgc tcg tgg atc cga gca caa gct        309
Gly Phe Asp Glu Thr Asp Leu His Arg Ser Trp Ile Arg Ala Gln Ala
 50                  55                  60 act cgg agt ccg cag gag agg aat act agg ctc gag aat atg tgc tgg        357
Thr Arg Ser Pro Gln Glu Arg Asn Thr Arg Leu Glu Asn Met Cys Trp
 65                  70                  75                  80 agg att tgg aat ttg gct cgc cag aaa aag cag ctt gag gga gag caa        405
Arg Ile Trp Asn Leu Ala Arg Gln Lys Lys Gln Leu Glu Gly Glu Gln
             85                  90                  95 gct cag tgg atg gca aaa cgc cgt caa gaa cgt gag aga ggt cgc aga        453
Ala Gln Trp Met Ala Lys Arg Arg Gln Glu Arg Glu Arg Gly Arg Arg
            100                 105                 110 gaa gca gtt gct gat atg tca gag gat cta tct gag gga gag aaa gga        501
Glu Ala Val Ala Asp Met Ser Glu Asp Leu Ser Glu Gly Glu Lys Gly
            115                 120                 125 gat ata gtc gct gac atg tca tct cat ggt gaa agt acc aga ggc cga        549
Asp Ile Val Ala Asp Met Ser Ser His Gly Glu Ser Thr Arg Gly Arg
130                 135                 140 ttg cct aga atc agt tct gtt gag aca atg gaa gca tgg gtc agt cag        597
Leu Pro Arg Ile Ser Ser Val Glu Thr Met Glu Ala Trp Val Ser Gln
145                 150                 155                 160 cag aga gga aag aag ctt tat atc gtg ctt ata agt tta cat ggt tta        645
Gln Arg Gly Lys Lys Leu Tyr Ile Val Leu Ile Ser Leu His Gly Leu
                165                 170                 175 att cgg ggt gag aat atg gag ctt gga cgg gat tct gat act ggt ggt        693
Ile Arg Gly Glu Asn Met Glu Leu Gly Arg Asp Ser Asp Thr Gly Gly
            180                 185                 190 cag gtg aag tat gta gtt gga gca act gtt gca caa ggt cgt ttg tca        741
Gln Val Lys Tyr Val Val Gly Ala Thr Val Ala Gln Gly Arg Leu Ser
            195                 200                 205 aag gat gaa ata aac tca acc tac aag ata atg cgg aga ata gag gct        789
Lys Asp Glu Ile Asn Ser Thr Tyr Lys Ile Met Arg Arg Ile Glu Ala
    210                 215                 220 gaa gaa tta act ctt gat gct tcc gaa att gtc atc act agt aca aga        837
Glu Glu Leu Thr Leu Asp Ala Ser Glu Ile Val Ile Thr Ser Thr Arg
225                 230                 235                 240 cag gag att gac gag caa tgg cgt ttg tat gat ggg ttt gat cca ata        885
Gln Glu Ile Asp Glu Gln Trp Arg Leu Tyr Asp Gly Phe Asp Pro Ile
                245                 250                 255 tta gag cgt aag tta cgt gca agg atc aag cgc aat gtc agc tgt tat        933
Leu Glu Arg Lys Leu Arg Ala Arg Ile Lys Arg Asn Val Ser Cys Tyr
            260                 265                 270 ggc agg ttt atg cct cgt atg gct gta att cct cct ggg atg gag ttc        981
Gly Arg Phe Met Pro Arg Met Ala Val Ile Pro Pro Gly Met Glu Phe
            275                 280                 285 cac cat att gtg cca cat gaa ggt gac atg gat ggt gaa aca gaa gga       1029
His His Ile Val Pro His Glu Gly Asp Met Asp Gly Glu Thr Glu Gly
        290                 295                 300 agt gaa gat gga aag acc ccg gat cca cct att tgg gca gag att atg       1077
Ser Glu Asp Gly Lys Thr Pro Asp Pro Pro Ile Trp Ala Glu Ile Met
305                 310                 315                 320 cgc ttc ttt tct aat cca agg aag cct atg ata ctc gca ctt gct agg       1125
Arg Phe Phe Ser Asn Pro Arg Lys Pro Met Ile Leu Ala Leu Ala Arg
                325                 330                 335 cct gat ccc aag aag aac ctc act act tta gtg aaa gca ttt ggt gaa       1173
Pro Asp Pro Lys Lys Asn Leu Thr Thr Leu Val Lys Ala Phe Gly Glu
```

```
                                                                    -continued Pro Asp Pro Lys Lys Asn Leu Thr Thr Leu Val Lys Ala Phe Gly Glu
        340                 345                 350 tgt cgt cca ttg aga gac ctt gct aat ctt act ttg ata atg ggt aat    1221
Cys Arg Pro Leu Arg Asp Leu Ala Asn Leu Thr Leu Ile Met Gly Asn
        355                 360                 365 cga gat aat atc gac gaa atg tct agc acc aat tct gca ctt ctt ctt    1269
Arg Asp Asn Ile Asp Glu Met Ser Ser Thr Asn Ser Ala Leu Leu Leu
        370                 375                 380 tca atc ttg aag atg ata gat aag tat gat ctt tat ggt cta gta gct    1317
Ser Ile Leu Lys Met Ile Asp Lys Tyr Asp Leu Tyr Gly Leu Val Ala
385                 390                 395                 400 tat cct aaa cac cac aag cag tca gat gtt cct gat atc tac cgt ctt    1365
Tyr Pro Lys His His Lys Gln Ser Asp Val Pro Asp Ile Tyr Arg Leu
                405                 410                 415 gct gca aag act aag ggt gtt ttt att aat cca gct ttt att gag cct    1413
Ala Ala Lys Thr Lys Gly Val Phe Ile Asn Pro Ala Phe Ile Glu Pro
        420                 425                 430 ttt gga ctg act ttg att gag gca gca gct tat ggt ctc cca atg gta    1461
Phe Gly Leu Thr Leu Ile Glu Ala Ala Ala Tyr Gly Leu Pro Met Val
        435                 440                 445 gcc aca aaa aat gga gga cct gtt gat ata cat agg gtt ctt gac aat    1509
Ala Thr Lys Asn Gly Gly Pro Val Asp Ile His Arg Val Leu Asp Asn
        450                 455                 460 ggt ctc tta gtg gat ccc cat gat cag cag gca att gct gat gct ctt    1557
Gly Leu Leu Val Asp Pro His Asp Gln Gln Ala Ile Ala Asp Ala Leu
465                 470                 475                 480 ttg aag ttg gtt gct gat aag caa ctg tgg gct aaa tgc agg gca aat    1605
Leu Lys Leu Val Ala Asp Lys Gln Leu Trp Ala Lys Cys Arg Ala Asn
                485                 490                 495 gga tta aaa aat atc cac ctt ttc tca tgg ccc gag cac tgt aaa act    1653
Gly Leu Lys Asn Ile His Leu Phe Ser Trp Pro Glu His Cys Lys Thr
        500                 505                 510 tat cta tcc cgg ata gct agc tgc aaa ccg agg caa cat tcc ttg aga    1701
Tyr Leu Ser Arg Ile Ala Ser Cys Lys Pro Arg Gln His Ser Leu Arg
        515                 520                 525 gat att cat gat ata tct ctg aat ttg aga ttt tca tta gat ggg gaa    1749
Asp Ile His Asp Ile Ser Leu Asn Leu Arg Phe Ser Leu Asp Gly Glu
        530                 535                 540 aag aat gac aat aaa gaa aat gct gat aat aca tta gac ccc gaa gtt    1797
Lys Asn Asp Asn Lys Glu Asn Ala Asp Asn Thr Leu Asp Pro Glu Val
545                 550                 555                 560 cga agg agc aag tta gag aat gct gtt ttg tcc tta tct aag ggt gca    1845
Arg Arg Ser Lys Leu Glu Asn Ala Val Leu Ser Leu Ser Lys Gly Ala
                565                 570                 575 ctg aag agc aca tca aaa tct tgg tcg tca gac aag gca gac caa aat    1893
Leu Lys Ser Thr Ser Lys Ser Trp Ser Ser Asp Lys Ala Asp Gln Asn
        580                 585                 590 cct ggt gct ggt aaa ttc cca gcg att agg agg agg cga cat att ttt    1941
Pro Gly Ala Gly Lys Phe Pro Ala Ile Arg Arg Arg Arg His Ile Phe
        595                 600                 605 gtt att gca gtg gat tgt gat gct agc tca gga ctc tct gga agt atg    1989
Val Ile Ala Val Asp Cys Asp Ala Ser Ser Gly Leu Ser Gly Ser Met
        610                 615                 620 aaa aag ata ttt gag gct gta gag aag gaa agg gca gag ggt tcc att    2037
Lys Lys Ile Phe Glu Ala Val Glu Lys Glu Arg Ala Glu Gly Ser Ile
625                 630                 635                 640 gga ttt atc ctt gct aca tct ttc aat ata tca gaa gta cag tct ttc    2085
Gly Phe Ile Leu Ala Thr Ser Phe Asn Ile Ser Glu Val Gln Ser Phe
                645                 650                 655
```

```
ctg ctt tca gag ggc atg aat cct act gag caa aat cct ttt gta gtt      2133
Leu Leu Ser Glu Gly Met Asn Pro Thr Glu Gln Asn Pro Phe Val Val
            660                 665                 670 gac ttg tac tat cac tca cat att gag tat cgt tgg ggg ggc gaa ggg      2181
Asp Leu Tyr Tyr His Ser His Ile Glu Tyr Arg Trp Gly Gly Glu Gly
            675                 680                 685 ttg aga aag act ttg gtg cgt tgg gcc gcc tct atc att gat aag aat      2229
Leu Arg Lys Thr Leu Val Arg Trp Ala Ala Ser Ile Ile Asp Lys Asn
690                 695                 700 ggt gaa aat gga gat cac att gtt gtt gag gat gaa gac aat tca gct      2277
Gly Glu Asn Gly Asp His Ile Val Val Glu Asp Glu Asp Asn Ser Ala
705                 710                 715                 720 gac tac tgc tat aca ttc aaa gtt tgc aag cct ggg acg gtt cct cca      2325
Asp Tyr Cys Tyr Thr Phe Lys Val Cys Lys Pro Gly Thr Val Pro Pro
                725                 730                 735 tct aaa gaa ctt aga aaa gta atg cga att cag gca ctt cgt tgt cac      2373
Ser Lys Glu Leu Arg Lys Val Met Arg Ile Gln Ala Leu Arg Cys His
            740                 745                 750 gct gtt tat tgt caa aat ggg agt agg att aat gtg atc cct gta ctg      2421
Ala Val Tyr Cys Gln Asn Gly Ser Arg Ile Asn Val Ile Pro Val Leu
            755                 760                 765 gca tct cgg tcc caa gca ctc agg tac tta tat ctg cga tgg gga atg      2469
Ala Ser Arg Ser Gln Ala Leu Arg Tyr Leu Tyr Leu Arg Trp Gly Met
770                 775                 780 gtc cct gta ctg gca tct cgg tcc caa gca ctc agg tac tta tat ctg      2517
Val Pro Val Leu Ala Ser Arg Ser Gln Ala Leu Arg Tyr Leu Tyr Leu
785                 790                 795                 800 cga tgg gga atg gtc cct gta ctg gca tct cgg tcc caa gca ctc agg      2565
Arg Trp Gly Met Val Pro Val Leu Ala Ser Arg Ser Gln Ala Leu Arg
                805                 810                 815 tac tta tat ctg cga tgg gga atg gac ttg tcg aag ttg gtg gtt ttc      2613
Tyr Leu Tyr Leu Arg Trp Gly Met Asp Leu Ser Lys Leu Val Val Phe
            820                 825                 830 gtc gga gaa agt ggt gat acc gat tat gaa gga ttg atc ggt ggt cta      2661
Val Gly Glu Ser Gly Asp Thr Asp Tyr Glu Gly Leu Ile Gly Gly Leu
            835                 840                 845 cgc aag gct gtc ata atg aaa gga ctc tgc act aat gca agc agc tta      2709
Arg Lys Ala Val Ile Met Lys Gly Leu Cys Thr Asn Ala Ser Ser Leu
850                 855                 860 att cac ggt aat agg aat tac ccg cta tct gat gtt tta cca ttc gag      2757
Ile His Gly Asn Arg Asn Tyr Pro Leu Ser Asp Val Leu Pro Phe Glu
865                 870                 875                 880 agc cct aat gtc atc caa gcg gat gag gaa tgt agc agc acc gga atc      2805
Ser Pro Asn Val Ile Gln Ala Asp Glu Glu Cys Ser Ser Thr Gly Ile
                885                 890                 895 cgt tcc tta ctg gag aaa cta gcg gta ctc aaa gga taatacccct           2851
Arg Ser Leu Leu Glu Lys Leu Ala Val Leu Lys Gly
            900                 905 ccccctttga ttgtcaaaaa cctatatgag ctaagattat gccatgaaaa gaatggccat    2911
ccatttggct tgtcttttg                                                 2930

<210> SEQ ID NO 6
<211> LENGTH: 908
<212> TYPE: PRT
<213> ORGANISM: Solanum tuberosum

<400> SEQUENCE: 6

Met Ala Gly Asn Asp Trp Ile Asn Ser Tyr Leu Glu Ala Ile Leu Asp
 1               5                   10                  15
```

-continued

Val Gly Pro Gly Leu Asp Asp Lys Lys Ser Leu Leu Arg Glu
          20                  25                  30

Arg Gly Arg Phe Ser Pro Thr Arg Tyr Phe Val Glu Glu Val Ile Thr
          35                  40                  45

Gly Phe Asp Glu Thr Asp Leu His Arg Ser Trp Ile Arg Ala Gln Ala
          50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Gly Glu Gln
              85                  90                  95

Ala Gln Trp Met Ala Lys Arg Arg Gln Glu Arg Glu Arg Gly Arg Arg
              100                 105                 110

Glu Ala Val Ala Asp Met Ser Glu Asp Leu Ser Glu Gly Glu Lys Gly
          115                 120                 125

Asp Ile Val Ala Asp Met Ser Ser His Gly Glu Ser Thr Arg Gly Arg
          130                 135                 140

Leu Pro Arg Ile Ser Ser Val Glu Thr Met Glu Ala Trp Val Ser Gln
145                 150                 155                 160

Gln Arg Gly Lys Lys Leu Tyr Ile Val Leu Ile Ser Leu His Gly Leu
              165                 170                 175

Ile Arg Gly Glu Asn Met Glu Leu Gly Arg Asp Ser Asp Thr Gly Gly
          180                 185                 190

Gln Val Lys Tyr Val Val Gly Ala Thr Val Ala Gln Gly Arg Leu Ser
          195                 200                 205

Lys Asp Glu Ile Asn Ser Thr Tyr Lys Ile Met Arg Arg Ile Glu Ala
210                 215                 220

Glu Glu Leu Thr Leu Asp Ala Ser Glu Ile Val Ile Thr Ser Thr Arg
225                 230                 235                 240

Gln Glu Ile Asp Glu Gln Trp Arg Leu Tyr Asp Gly Phe Asp Pro Ile
              245                 250                 255

Leu Glu Arg Lys Leu Arg Ala Arg Ile Lys Arg Asn Val Ser Cys Tyr
              260                 265                 270

Gly Arg Phe Met Pro Arg Met Ala Val Ile Pro Pro Gly Met Glu Phe
          275                 280                 285

His His Ile Val Pro His Glu Gly Asp Met Asp Gly Glu Thr Glu Gly
          290                 295                 300

Ser Glu Asp Gly Lys Thr Pro Asp Pro Ile Trp Ala Glu Ile Met
305                 310                 315                 320

Arg Phe Phe Ser Asn Pro Arg Lys Pro Met Ile Leu Ala Leu Ala Arg
              325                 330                 335

Pro Asp Pro Lys Lys Asn Leu Thr Thr Leu Val Lys Ala Phe Gly Glu
              340                 345                 350

Cys Arg Pro Leu Arg Asp Leu Ala Asn Leu Thr Leu Ile Met Gly Asn
              355                 360                 365

Arg Asp Asn Ile Asp Glu Met Ser Ser Thr Asn Ser Ala Leu Leu Leu
          370                 375                 380

Ser Ile Leu Lys Met Ile Asp Lys Tyr Asp Leu Tyr Gly Leu Val Ala
385                 390                 395                 400

Tyr Pro Lys His His Lys Gln Ser Asp Val Pro Asp Ile Tyr Arg Leu
              405                 410                 415

Ala Ala Lys Thr Lys Gly Val Phe Ile Asn Pro Ala Phe Ile Glu Pro
          420                 425                 430

Phe Gly Leu Thr Leu Ile Glu Ala Ala Ala Tyr Gly Leu Pro Met Val

-continued

```
                435                 440                 445
Ala Thr Lys Asn Gly Gly Pro Val Asp Ile His Arg Val Leu Asp Asn
    450                 455                 460
Gly Leu Leu Val Asp Pro His Asp Gln Gln Ala Ile Ala Asp Ala Leu
465                 470                 475                 480
Leu Lys Leu Val Ala Asp Lys Gln Leu Trp Ala Lys Cys Arg Ala Asn
                485                 490                 495
Gly Leu Lys Asn Ile His Leu Phe Ser Trp Pro Glu His Cys Lys Thr
            500                 505                 510
Tyr Leu Ser Arg Ile Ala Ser Cys Lys Pro Arg Gln His Ser Leu Arg
            515                 520                 525
Asp Ile His Asp Ile Ser Leu Asn Leu Arg Phe Ser Leu Asp Gly Glu
        530                 535                 540
Lys Asn Asp Asn Lys Glu Asn Ala Asp Asn Thr Leu Asp Pro Glu Val
545                 550                 555                 560
Arg Arg Ser Lys Leu Glu Asn Ala Val Leu Ser Leu Ser Lys Gly Ala
                565                 570                 575
Leu Lys Ser Thr Ser Lys Ser Trp Ser Ser Asp Lys Ala Asp Gln Asn
            580                 585                 590
Pro Gly Ala Gly Lys Phe Pro Ala Ile Arg Arg Arg His Ile Phe
            595                 600                 605
Val Ile Ala Val Asp Cys Asp Ala Ser Ser Gly Leu Ser Gly Ser Met
        610                 615                 620
Lys Lys Ile Phe Glu Ala Val Glu Lys Glu Arg Ala Glu Gly Ser Ile
625                 630                 635                 640
Gly Phe Ile Leu Ala Thr Ser Phe Asn Ile Ser Glu Val Gln Ser Phe
                645                 650                 655
Leu Leu Ser Glu Gly Met Asn Pro Thr Glu Gln Asn Pro Phe Val Val
            660                 665                 670
Asp Leu Tyr Tyr His Ser His Ile Glu Tyr Arg Trp Gly Gly Glu Gly
            675                 680                 685
Leu Arg Lys Thr Leu Val Arg Trp Ala Ala Ser Ile Ile Asp Lys Asn
        690                 695                 700
Gly Glu Asn Gly Asp His Ile Val Val Glu Asp Glu Asp Asn Ser Ala
705                 710                 715                 720
Asp Tyr Cys Tyr Thr Phe Lys Val Cys Lys Pro Gly Thr Val Pro Pro
                725                 730                 735
Ser Lys Glu Leu Arg Lys Val Met Arg Ile Gln Ala Leu Arg Cys His
            740                 745                 750
Ala Val Tyr Cys Gln Asn Gly Ser Arg Ile Asn Val Ile Pro Val Leu
            755                 760                 765
Ala Ser Arg Ser Gln Ala Leu Arg Tyr Leu Tyr Leu Arg Trp Gly Met
        770                 775                 780
Val Pro Val Leu Ala Ser Arg Ser Gln Ala Leu Arg Tyr Leu Tyr Leu
785                 790                 795                 800
Arg Trp Gly Met Val Pro Val Leu Ala Ser Arg Ser Gln Ala Leu Arg
                805                 810                 815
Tyr Leu Tyr Leu Arg Trp Gly Met Asp Leu Ser Lys Leu Val Val Phe
            820                 825                 830
Val Gly Glu Ser Gly Asp Thr Asp Tyr Glu Gly Leu Ile Gly Gly Leu
            835                 840                 845
Arg Lys Ala Val Ile Met Lys Gly Leu Cys Thr Asn Ala Ser Ser Leu
        850                 855                 860
```

-continued

```
Ile His Gly Asn Arg Asn Tyr Pro Leu Ser Asp Val Leu Pro Phe Glu
865                 870             875                 880

Ser Pro Asn Val Ile Gln Ala Asp Glu Glu Cys Ser Ser Thr Gly Ile
                885             890                 895

Arg Ser Leu Leu Glu Lys Leu Ala Val Leu Lys Gly
            900             905
```